US008226552B2

(12) United States Patent
Albrecht et al.

(10) Patent No.: US 8,226,552 B2
(45) Date of Patent: *Jul. 24, 2012

(54) SURGICAL RETRACTOR

(75) Inventors: Jeremy J. Albrecht, Ladera Ranch, CA (US); Jennifer T. Ko, Rancho Santa Margarita, CA (US); Gary M. Johnson, Mission Viejo, CA (US); John R. Brustad, Dana Point, CA (US); Kevin K. Dang, Garden Grove, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 1108 days.

This patent is subject to a terminal disclaimer.

(21) Appl. No.: 12/119,414

(22) Filed: May 12, 2008

(65) Prior Publication Data

US 2008/0281162 A1 Nov. 13, 2008

Related U.S. Application Data

(60) Provisional application No. 60/917,571, filed on May 11, 2007.

(51) Int. Cl.
*A61B 1/32* (2006.01)
(52) U.S. Cl. ...................................... 600/208
(58) Field of Classification Search ............. 600/201, 600/204, 205, 206, 208, 209
See application file for complete search history.

(56) References Cited

U.S. PATENT DOCUMENTS

| | | | |
|---|---|---|---|
| 558,364 A | 4/1896 | Doolittle | |
| 1,157,202 A | 10/1915 | Bates et al. | |
| 1,598,284 A | 8/1926 | Kinney | |
| 1,690,995 A | 11/1928 | Pratt | |
| 1,180,466 A | 6/1931 | Deutsch | |
| 1,810,466 A | 6/1931 | Deutsch | |
| 2,219,564 A | 10/1940 | Reyniers | |
| 2,305,289 A | 12/1942 | Coburg | |
| 2,478,586 A | 8/1949 | Krapp | |
| 2,669,991 A | 2/1954 | Curutchet | |
| 2,695,608 A | 11/1954 | Gibbon | |
| 2,812,758 A | 11/1957 | Blumenschein | |

(Continued)

FOREIGN PATENT DOCUMENTS

DE 26 05 148 A1 8/1977

(Continued)

OTHER PUBLICATIONS

The International Searching Authority, The International Search Report and Written Opinion of the International Searching Authority for International Application No. PCT/US08/63445, mailed Sep. 29, 2008.

(Continued)

*Primary Examiner* — Anu Ramana
(74) *Attorney, Agent, or Firm* — Patrick Y. Ikehara; Pui Tong Ho

(57) ABSTRACT

A surgical access device has a surgical retractor having a noncompliant outer ring with an annular axis, an inner ring, and a sleeve coupling the outer ring to the inner ring. The noncompliant outer ring is adapted to roll over itself around the annular axis to roll the sleeve around the outer ring to retract and seal an opening in a biological body wall. The access device may include a lid adapted for being coupled to the noncompliant outer ring of the surgical retractor. The outer ring of the surgical retractor has a cross-sectional shape that prohibits the lid from being partially or incorrectly coupled to the outer ring of the surgical retractor.

11 Claims, 8 Drawing Sheets

U.S. PATENT DOCUMENTS

| | | |
|---|---|---|
| 2,835,253 A | 5/1958 | Borgeson |
| 2,853,075 A | 9/1958 | Hoffman et al. |
| 3,039,468 A | 6/1962 | Price |
| 3,057,350 A | 10/1962 | Cowley |
| 3,111,943 A | 11/1963 | Orndorff |
| 3,195,934 A | 7/1965 | Parrish |
| 3,244,169 A | 4/1966 | Baxter |
| 3,253,594 A | 5/1966 | Matthews et al. |
| 3,313,299 A | 4/1967 | Spademan |
| 3,329,390 A | 7/1967 | Hulsey |
| 3,332,417 A | 7/1967 | Blanford et al. |
| 3,347,226 A | 10/1967 | Harrower |
| 3,347,227 A | 10/1967 | Harrower |
| 3,397,692 A | 8/1968 | Creager, Jr. et al. |
| 3,402,710 A | 9/1968 | Paleschuck |
| 3,416,520 A | 12/1968 | Creager, Jr. |
| 3,447,533 A | 6/1969 | Spicer |
| 3,522,800 A | 8/1970 | Lesser |
| 3,523,534 A | 8/1970 | Nolan |
| 3,570,475 A | 3/1971 | Weinstein |
| 3,656,485 A | 4/1972 | Robertson |
| 3,685,786 A | 8/1972 | Woodson |
| 3,717,151 A | 2/1973 | Collett |
| 3,717,883 A | 2/1973 | Mosher |
| 3,729,006 A | 4/1973 | Wilder et al. |
| 3,782,370 A | 1/1974 | McDonald |
| 3,797,478 A | 3/1974 | Walsh et al. |
| 3,799,166 A | 3/1974 | Marsan |
| 3,807,393 A | 4/1974 | McDonald |
| 3,828,764 A | 8/1974 | Jones |
| 3,831,583 A | 8/1974 | Edmunds et al. |
| 3,841,332 A | 10/1974 | Treacle |
| 3,850,172 A | 11/1974 | Cazalis |
| 3,853,126 A | 12/1974 | Schulte |
| 3,853,127 A | 12/1974 | Spademan |
| 3,856,021 A | 12/1974 | McIntosh |
| 3,860,274 A | 1/1975 | Ledstrom et al. |
| 3,861,416 A | 1/1975 | Wichterle |
| 3,907,389 A | 9/1975 | Cox et al. |
| 3,915,171 A | 10/1975 | Shermeta |
| 3,965,890 A | 6/1976 | Gauthier |
| 3,970,089 A | 7/1976 | Saice |
| 3,996,623 A | 12/1976 | Kaster |
| 4,000,739 A | 1/1977 | Stevens |
| 4,016,884 A | 4/1977 | Kwan-Gett |
| 4,024,872 A | 5/1977 | Muldoon |
| 4,030,500 A | 6/1977 | Ronnquist |
| 4,043,328 A | 8/1977 | Cawood, Jr. et al. |
| 4,069,913 A | 1/1978 | Harrigan |
| 4,082,005 A | 4/1978 | Erdley |
| 4,083,370 A | 4/1978 | Taylor |
| 4,096,853 A | 6/1978 | Weigand |
| 4,112,932 A | 9/1978 | Chiulli |
| 4,130,113 A | 12/1978 | Graham |
| 4,177,814 A | 12/1979 | Knepshield et al. |
| 4,183,357 A | 1/1980 | Bentley et al. |
| 4,187,849 A | 2/1980 | Stim |
| 4,188,945 A | 2/1980 | Wenander |
| 4,217,664 A | 8/1980 | Faso |
| 4,222,126 A | 9/1980 | Boretos et al. |
| 4,228,792 A | 10/1980 | Rhys-Davies |
| 4,239,036 A | 12/1980 | Krieger |
| 4,240,411 A | 12/1980 | Hosono |
| 4,253,201 A | 3/1981 | Ross et al. |
| 4,254,973 A | 3/1981 | Benjamin |
| 4,306,562 A | 12/1981 | Osborne |
| 4,321,915 A | 3/1982 | Leighton |
| 4,331,138 A | 5/1982 | Jessen |
| 4,338,934 A | 7/1982 | Spademan |
| 4,338,937 A | 7/1982 | Lerman |
| 4,367,728 A | 1/1983 | Mutke |
| 4,369,284 A | 1/1983 | Chen |
| 4,399,816 A | 8/1983 | Spangler |
| 4,402,683 A | 9/1983 | Kopman |
| 4,411,659 A | 10/1983 | Jensen et al. |
| 4,421,296 A | 12/1983 | Stephens |
| 4,424,833 A | 1/1984 | Spector et al. |
| 4,428,364 A | 1/1984 | Bartolo |
| 4,430,081 A | 2/1984 | Timmermans |
| 4,434,791 A | 3/1984 | Darnell |
| 4,436,519 A | 3/1984 | O'Neill |
| 4,454,873 A | 6/1984 | Laufenberg et al. |
| 4,473,067 A | 9/1984 | Schiff |
| 4,475,548 A | 10/1984 | Muto |
| 4,485,490 A | 12/1984 | Akers et al. |
| 4,488,877 A | 12/1984 | Klein |
| 4,543,088 A | 9/1985 | Bootman et al. |
| 4,550,713 A | 11/1985 | Hyman |
| 4,553,537 A | 11/1985 | Rosenberg |
| 4,555,242 A | 11/1985 | Saudagar |
| 4,556,996 A | 12/1985 | Wallace |
| 4,601,710 A | 7/1986 | Moll |
| 4,610,665 A | 9/1986 | Matsumoto et al. |
| 4,626,245 A | 12/1986 | Weinstein |
| 4,634,424 A | 1/1987 | O'Boyle |
| 4,634,432 A | 1/1987 | Kocak |
| 4,644,951 A | 2/1987 | Bays |
| 4,649,904 A | 3/1987 | Krauter |
| 4,653,476 A | 3/1987 | Bonnet |
| 4,654,030 A | 3/1987 | Moll et al. |
| 4,655,752 A | 4/1987 | Honkanen et al. |
| 4,673,393 A | 6/1987 | Suzuki et al. |
| 4,673,394 A | 6/1987 | Fenton |
| 4,691,942 A | 9/1987 | Ford |
| 4,714,749 A | 12/1987 | Hughes et al. |
| 4,738,666 A | 4/1988 | Fuqua |
| 4,755,170 A | 7/1988 | Golden |
| 4,760,933 A | 8/1988 | Christner et al. |
| 4,776,843 A | 10/1988 | Martinez et al. |
| 4,777,943 A | 10/1988 | Chvapil |
| 4,784,646 A | 11/1988 | Feingold |
| 4,796,629 A | 1/1989 | Grayzel |
| 4,798,594 A | 1/1989 | Hillstead |
| 4,802,694 A | 2/1989 | Vargo |
| 4,808,168 A | 2/1989 | Warring |
| 4,809,679 A | 3/1989 | Shimonaka et al. |
| 4,828,554 A | 5/1989 | Griffin |
| 4,842,931 A | 6/1989 | Zook |
| 4,848,575 A | 7/1989 | Nakamura et al. |
| 4,856,502 A | 8/1989 | Ersfeld et al. |
| 4,863,430 A | 9/1989 | Klyce et al. |
| 4,863,438 A | 9/1989 | Gauderer et al. |
| 4,889,107 A | 12/1989 | Kaufman |
| 4,895,565 A | 1/1990 | Hillstead |
| 4,897,081 A | 1/1990 | Poirier |
| 4,903,710 A | 2/1990 | Jessamine et al. |
| 4,911,974 A | 3/1990 | Shimizu et al. |
| 4,915,132 A | 4/1990 | Hodge et al. |
| 4,926,882 A | 5/1990 | Lawrence |
| 4,929,235 A | 5/1990 | Merry et al. |
| 4,944,732 A | 7/1990 | Russo |
| 4,950,222 A | 8/1990 | Scott et al. |
| 4,950,223 A | 8/1990 | Silvanov |
| 4,984,564 A | 1/1991 | Yuen |
| 4,991,593 A | 2/1991 | LeVahn |
| 4,998,538 A | 3/1991 | Charowsky et al. |
| 5,000,745 A | 3/1991 | Guest et al. |
| 5,009,224 A | 4/1991 | Cole |
| 5,015,228 A | 5/1991 | Columbus et al. |
| 5,019,101 A | 5/1991 | Purkait et al. |
| 5,026,366 A | 6/1991 | Leckrone |
| 5,037,379 A | 8/1991 | Clayman et al. |
| 5,041,095 A | 8/1991 | Littrell |
| 5,045,070 A | 9/1991 | Grodecki et al. |
| D320,658 S | 10/1991 | Quigley et al. |
| 5,071,411 A | 12/1991 | Hillstead |
| 5,073,169 A | 12/1991 | Raiken |
| 5,074,878 A | 12/1991 | Bark et al. |
| 5,082,005 A | 1/1992 | Kaldany |
| 5,086,763 A | 2/1992 | Hathman |
| 5,092,846 A | 3/1992 | Nishijima et al. |
| 5,104,389 A | 4/1992 | Deem |
| 5,125,396 A | 6/1992 | Ray |
| 5,125,897 A | 6/1992 | Quinn et al. |
| 5,127,626 A | 7/1992 | Hilal et al. |
| 5,129,885 A | 7/1992 | Green et al. |
| 5,141,498 A | 8/1992 | Christian |

| | | |
|---|---|---|
| 5,149,327 A | 9/1992 | Oshiyama |
| 5,156,617 A | 10/1992 | Reid |
| 5,158,553 A | 10/1992 | Berry et al. |
| 5,159,921 A | 11/1992 | Hoover |
| 5,161,773 A | 11/1992 | Tower |
| 5,167,636 A | 12/1992 | Clement |
| 5,167,637 A | 12/1992 | Okada et al. |
| 5,176,648 A | 1/1993 | Holmes et al. |
| 5,176,662 A | 1/1993 | Bartholomew et al. |
| 5,176,697 A | 1/1993 | Hasson et al. |
| 5,178,162 A | 1/1993 | Bose |
| 5,180,365 A | 1/1993 | Ensminger et al. |
| 5,183,471 A | 2/1993 | Wilk |
| 5,188,595 A | 2/1993 | Jacobi |
| 5,188,607 A | 2/1993 | Wu |
| 5,192,301 A | 3/1993 | Kamiya et al. |
| 5,197,955 A | 3/1993 | Stephens et al. |
| 5,207,656 A | 5/1993 | Kranys |
| 5,209,737 A | 5/1993 | Rirchart et al. |
| 5,211,370 A | 5/1993 | Powers |
| 5,211,633 A | 5/1993 | Stouder, Jr. |
| 5,213,114 A | 5/1993 | Bailey, Jr. |
| 5,226,890 A | 7/1993 | Ianniruberto et al. |
| 5,234,455 A | 8/1993 | Mulhollan |
| 5,241,968 A | 9/1993 | Slater |
| 5,242,400 A | 9/1993 | Buelna |
| 5,242,409 A | 9/1993 | Buelna |
| 5,242,412 A | 9/1993 | Blake, III |
| 5,242,415 A | 9/1993 | Kantrowitz et al. |
| 5,248,304 A | 9/1993 | Vigdorchik et al. |
| 5,256,150 A | 10/1993 | Quiachon et al. |
| 5,257,973 A | 11/1993 | Villasuso |
| 5,257,975 A | 11/1993 | Foshee |
| 5,259,366 A | 11/1993 | Reydel et al. |
| 5,261,883 A | 11/1993 | Hood et al. |
| 5,262,468 A | 11/1993 | Chen |
| 5,263,922 A | 11/1993 | Sova et al. |
| 5,269,763 A | 12/1993 | Boehmer et al. |
| 5,269,772 A | 12/1993 | Wilk |
| 5,273,449 A | 12/1993 | Mattis et al. |
| 5,273,545 A | 12/1993 | Hunt et al. |
| D343,236 S | 1/1994 | Quigley et al. |
| 5,279,575 A | 1/1994 | Sugarbaker |
| 5,290,310 A | 3/1994 | Makower et al. |
| D346,022 S | 4/1994 | Quigley et al. |
| 5,299,582 A | 4/1994 | Potts |
| 5,300,034 A | 4/1994 | Behnke |
| 5,300,035 A | 4/1994 | Clement |
| 5,300,036 A | 4/1994 | Mueller et al. |
| 5,308,336 A | 5/1994 | Hart et al. |
| 5,309,896 A | 5/1994 | Moll et al. |
| 5,312,391 A | 5/1994 | Wilk |
| 5,314,417 A | 5/1994 | Stephens et al. |
| 5,316,541 A | 5/1994 | Fischer |
| 5,320,611 A | 6/1994 | Bonutti et al. |
| 5,330,437 A | 7/1994 | Durman |
| 5,330,486 A | 7/1994 | Wilk |
| 5,330,497 A | 7/1994 | Freitas et al. |
| 5,331,975 A | 7/1994 | Bonutti |
| 5,334,143 A | 8/1994 | Carroll |
| 5,334,646 A | 8/1994 | Chen |
| 5,336,192 A | 8/1994 | Palestrant |
| 5,336,708 A | 8/1994 | Chen |
| 5,338,313 A | 8/1994 | Mollenauer et al. |
| 5,342,315 A | 8/1994 | Rowe et al. |
| 5,342,385 A | 8/1994 | Norelli et al. |
| 5,350,364 A | 9/1994 | Stephens et al. |
| 5,353,786 A | 10/1994 | Wilk |
| 5,354,280 A | 10/1994 | Haber et al. |
| 5,360,417 A | 11/1994 | Gravener et al. |
| 5,364,345 A | 11/1994 | Lowery et al. |
| 5,364,372 A | 11/1994 | Danks et al. |
| 5,366,446 A | 11/1994 | Tal et al. |
| 5,366,478 A | 11/1994 | Brinkerhoff et al. |
| 5,368,545 A | 11/1994 | Schaller et al. |
| 5,375,588 A | 12/1994 | Yoon |
| 5,380,288 A | 1/1995 | Hart et al. |
| 5,383,861 A | 1/1995 | Hempel et al. |
| 5,385,552 A | 1/1995 | Haber et al. |
| 5,385,553 A | 1/1995 | Hart et al. |
| 5,385,560 A | 1/1995 | Wulf |
| 5,389,080 A | 2/1995 | Yoon |
| 5,389,081 A | 2/1995 | Castro |
| 5,391,153 A | 2/1995 | Haber et al. |
| 5,391,156 A | 2/1995 | Hildwein et al. |
| 5,395,367 A | 3/1995 | Wilk |
| 5,403,264 A | 4/1995 | Wohlers et al. |
| 5,403,336 A | 4/1995 | Kieturakis et al. |
| 5,407,433 A | 4/1995 | Loomas |
| 5,411,483 A | 5/1995 | Loomas |
| 5,413,571 A | 5/1995 | Katsaros et al. |
| 5,423,848 A | 6/1995 | Washizuka et al. |
| 5,429,609 A | 7/1995 | Yoon |
| 5,431,676 A | 7/1995 | Dubrul et al. |
| 5,437,683 A | 8/1995 | Neumann et al. |
| 5,439,455 A | 8/1995 | Kieturakis et al. |
| 5,441,486 A | 8/1995 | Yoon |
| 5,443,452 A | 8/1995 | Hart et al. |
| 5,456,284 A | 10/1995 | Ryan et al. |
| 5,460,170 A | 10/1995 | Hammerslag |
| 5,460,616 A | 10/1995 | Weinstein et al. |
| 5,468,248 A | 11/1995 | Chin et al. |
| 5,476,475 A | 12/1995 | Gadberry |
| 5,480,410 A | 1/1996 | Cuschieri et al. |
| 5,486,426 A | 1/1996 | McGee et al. |
| 5,490,843 A | 2/1996 | Hildwein et al. |
| 5,492,304 A | 2/1996 | Smith et al. |
| 5,496,280 A | 3/1996 | Vandenbroek et al. |
| 5,503,112 A | 4/1996 | Luhman et al. |
| 5,507,758 A | 4/1996 | Thomason et al. |
| 5,508,334 A | 4/1996 | Chen |
| 5,511,564 A | 4/1996 | Wilk |
| 5,514,109 A | 5/1996 | Mollenauer et al. |
| 5,514,133 A | 5/1996 | Golub et al. |
| 5,514,153 A | 5/1996 | Bonutti |
| 5,518,278 A | 5/1996 | Sampson |
| 5,520,632 A | 5/1996 | Leveen |
| 5,522,791 A | 6/1996 | Leyva |
| 5,522,824 A | 6/1996 | Ashby |
| 5,524,644 A | 6/1996 | Crook |
| 5,526,536 A | 6/1996 | Cartmill |
| 5,531,758 A | 7/1996 | Uschold et al. |
| 5,538,509 A | 7/1996 | Dunlap et al. |
| 5,540,648 A | 7/1996 | Yoon |
| 5,540,711 A | 7/1996 | Kieturakis et al. |
| 5,545,150 A | 8/1996 | Danks et al. |
| 5,545,179 A | 8/1996 | Williamson, IV |
| 5,549,563 A | 8/1996 | Kronner |
| 5,549,637 A | 8/1996 | Crainich |
| 5,554,124 A | 9/1996 | Alvarado |
| 5,562,632 A | 10/1996 | Davila et al. |
| 5,562,677 A | 10/1996 | Hildwein et al. |
| 5,562,688 A | 10/1996 | Riza |
| 5,571,115 A | 11/1996 | Nicholas |
| 5,571,137 A | 11/1996 | Marlow et al. |
| 5,575,799 A | 11/1996 | Bolanos et al. |
| 5,577,993 A | 11/1996 | Zhu et al. |
| 5,578,048 A | 11/1996 | Pasqualucci et al. |
| 5,580,344 A | 12/1996 | Hasson |
| 5,584,850 A | 12/1996 | Hart et al. |
| 5,601,579 A | 2/1997 | Semertzides |
| 5,601,581 A | 2/1997 | Fogarty et al. |
| 5,603,702 A | 2/1997 | Smith et al. |
| 5,607,443 A | 3/1997 | Kieturakis et al. |
| 5,620,415 A | 4/1997 | Lucey et al. |
| 5,620,420 A | 4/1997 | Kriesel |
| 5,628,732 A | 5/1997 | Antoon, Jr. et al. |
| 5,632,284 A | 5/1997 | Graether |
| 5,632,979 A | 5/1997 | Goldberg et al. |
| 5,634,911 A | 6/1997 | Hermann et al. |
| 5,634,936 A | 6/1997 | Linden et al. |
| 5,634,937 A | 6/1997 | Mollenauer et al. |
| 5,636,645 A | 6/1997 | Ou |
| 5,640,977 A | 6/1997 | Leahy et al. |
| 5,643,301 A | 7/1997 | Mollenauer |
| 5,649,550 A | 7/1997 | Crook |
| 5,651,771 A | 7/1997 | Tangherlini et al. |
| 5,653,705 A | 8/1997 | de la Torre et al. |

| | | | | | | |
|---|---|---|---|---|---|---|
| 5,657,963 A | 8/1997 | Hinchliffe et al. | | 5,957,913 A | 9/1999 | de la Torre et al. |
| 5,658,272 A | 8/1997 | Hasson | | 5,962,572 A | 10/1999 | Chen |
| 5,658,306 A | 8/1997 | Kieturakis | | 5,964,781 A | 10/1999 | Mollenauer et al. |
| 5,662,615 A | 9/1997 | Blake, III | | 5,976,174 A | 11/1999 | Ruiz |
| 5,672,168 A | 9/1997 | de la Torre et al. | | 5,989,232 A | 11/1999 | Yoon |
| 5,681,341 A | 10/1997 | Lunsford et al. | | 5,989,233 A | 11/1999 | Yoon |
| 5,683,378 A | 11/1997 | Christy | | 5,989,266 A | 11/1999 | Foster |
| 5,685,854 A | 11/1997 | Green et al. | | 5,993,471 A | 11/1999 | Riza et al. |
| 5,685,857 A | 11/1997 | Negus et al. | | 5,993,485 A | 11/1999 | Beckers |
| 5,697,914 A | 12/1997 | Brimhall | | 5,994,450 A | 11/1999 | Pearce |
| 5,707,703 A | 1/1998 | Rothrum et al. | | 5,997,515 A | 12/1999 | de la Torre et al. |
| 5,709,664 A | 1/1998 | Vandenbroek et al. | | 6,004,303 A | 12/1999 | Peterson |
| 5,713,858 A | 2/1998 | Heruth et al. | | 6,010,494 A | 1/2000 | Schafer et al. |
| 5,713,869 A | 2/1998 | Morejon | | 6,017,355 A | 1/2000 | Hessel et al. |
| 5,720,730 A | 2/1998 | Blake, III | | 6,018,094 A | 1/2000 | Fox |
| 5,725,536 A | 3/1998 | Oberlin et al. | | 6,024,736 A | 2/2000 | de la Torre et al. |
| 5,728,103 A | 3/1998 | Picha et al. | | 6,025,067 A | 2/2000 | Fay |
| 5,730,748 A | 3/1998 | Fogarty et al. | | 6,033,426 A | 3/2000 | Kaji |
| 5,735,791 A | 4/1998 | Alexander et al. | | 6,033,428 A | 3/2000 | Sardella |
| 5,738,628 A | 4/1998 | Sierocuk et al. | | 6,035,559 A | 3/2000 | Freed et al. |
| 5,741,234 A | 4/1998 | Aboul-Hosn | | 6,042,573 A | 3/2000 | Lucey |
| 5,741,298 A | 4/1998 | MacLeod | | 6,045,535 A | 4/2000 | Ben Nun |
| 5,743,884 A | 4/1998 | Hasson et al. | | 6,048,309 A | 4/2000 | Flom et al. |
| 5,749,882 A | 5/1998 | Hart et al. | | 6,050,871 A | 4/2000 | Chen |
| 5,755,660 A | 5/1998 | Tyagi | | 6,053,934 A | 4/2000 | Andrews et al. |
| 5,760,117 A | 6/1998 | Chen | | 6,059,806 A | 5/2000 | Moenning |
| 5,769,783 A | 6/1998 | Fowler | | 6,066,117 A | 5/2000 | Fox et al. |
| 5,782,812 A | 7/1998 | Hart et al. | | 6,068,639 A | 5/2000 | Fogarty et al. |
| 5,782,817 A | 7/1998 | Franzel et al. | | 6,077,288 A | 6/2000 | Shimomura |
| 5,782,859 A | 7/1998 | Nicholas et al. | | 6,086,603 A | 7/2000 | Termin et al. |
| 5,788,676 A | 8/1998 | Yoon | | 6,090,043 A | 7/2000 | Austin et al. |
| 5,792,119 A | 8/1998 | Marx | | 6,099,506 A | 8/2000 | Macoviak et al. |
| 5,795,290 A | 8/1998 | Bridges | | 6,110,154 A | 8/2000 | Shimomura et al. |
| 5,803,919 A | 9/1998 | Hart et al. | | 6,123,689 A | 9/2000 | To et al. |
| 5,803,921 A | 9/1998 | Bonadio | | 6,142,935 A | 11/2000 | Flom et al. |
| 5,803,923 A | 9/1998 | Singh-Derewa et al. | | 6,142,936 A | 11/2000 | Beane et al. |
| 5,807,350 A | 9/1998 | Diaz | | 6,149,642 A | 11/2000 | Gerhart et al. |
| 5,810,712 A | 9/1998 | Dunn | | 6,150,608 A | 11/2000 | Wambeke et al. |
| 5,810,721 A | 9/1998 | Mueller et al. | | 6,159,182 A | 12/2000 | Davis |
| 5,813,409 A | 9/1998 | Leahy et al. | | 6,162,172 A | 12/2000 | Cosgrove et al. |
| 5,814,026 A | 9/1998 | Yoon | | 6,162,196 A | 12/2000 | Hart et al. |
| 5,817,062 A | 10/1998 | Flom et al. | | 6,162,206 A | 12/2000 | Bindokas |
| 5,819,375 A | 10/1998 | Kastner | | 6,163,949 A | 12/2000 | Neuenschwander |
| 5,820,555 A | 10/1998 | Watkins, III et al. | | 6,164,279 A | 12/2000 | Tweedle |
| 5,820,600 A | 10/1998 | Carlson et al. | | 6,171,282 B1 | 1/2001 | Ragsdale |
| 5,830,191 A | 11/1998 | Hildwein et al. | | 6,183,486 B1 | 2/2001 | Snow et al. |
| 5,832,925 A | 11/1998 | Rothrum | | 6,197,002 B1 | 3/2001 | Peterson |
| 5,836,871 A | 11/1998 | Wallace et al. | | 6,217,555 B1 | 4/2001 | Hart et al. |
| 5,841,298 A | 11/1998 | Huang | | 6,217,590 B1 | 4/2001 | Levinson |
| 5,842,971 A | 12/1998 | Yoon | | 6,224,612 B1 | 5/2001 | Bates et al. |
| 5,848,992 A | 12/1998 | Hart et al. | | 6,228,063 B1 | 5/2001 | Aboul-Hosn |
| 5,853,395 A | 12/1998 | Crook et al. | | 6,238,373 B1 | 5/2001 | de la Torre et al. |
| 5,853,417 A | 12/1998 | Fogarty et al. | | 6,241,768 B1 | 6/2001 | Agarwal et al. |
| 5,857,461 A | 1/1999 | Levitsky et al. | | 6,254,533 B1 | 7/2001 | Fadem et al. |
| 5,860,995 A | 1/1999 | Berkelaar | | 6,254,534 B1 | 7/2001 | Butler et al. |
| 5,865,728 A | 2/1999 | Moll et al. | | 6,258,065 B1 | 7/2001 | Dennis et al. |
| 5,865,729 A | 2/1999 | Meehan et al. | | 6,264,604 B1 | 7/2001 | Kieturakis et al. |
| 5,865,807 A | 2/1999 | Blake, III | | 6,267,751 B1 | 7/2001 | Mangosong |
| 5,865,817 A | 2/1999 | Moenning et al. | | 6,276,661 B1 | 8/2001 | Laird |
| 5,871,474 A | 2/1999 | Hermann et al. | | 6,287,280 B1 | 9/2001 | Lampropoulos et al. |
| 5,876,413 A | 3/1999 | Fogarty et al. | | 6,315,770 B1 | 11/2001 | de la Torre et al. |
| 5,879,368 A | 3/1999 | Hoskin et al. | | 6,319,246 B1 | 11/2001 | de la Torre et al. |
| 5,882,344 A | 3/1999 | Strouder, Jr. | | 6,322,541 B2 | 11/2001 | West |
| 5,884,639 A | 3/1999 | Chen | | 6,325,384 B1 | 12/2001 | Berry, Sr. et al. |
| 5,894,843 A | 4/1999 | Benetti et al. | | 6,346,074 B1 | 2/2002 | Roth |
| 5,895,377 A | 4/1999 | Smith et al. | | 6,371,968 B1 | 4/2002 | Kogasaka et al. |
| 5,899,208 A | 5/1999 | Bonadio | | 6,382,211 B1 | 5/2002 | Crook |
| 5,899,913 A | 5/1999 | Fogarty et al. | | 6,383,162 B1 | 5/2002 | Sugarbaker |
| 5,904,703 A | 5/1999 | Gilson | | 6,391,043 B1 | 5/2002 | Moll et al. |
| 5,906,577 A | 5/1999 | Beane et al. | | 6,413,244 B1 | 7/2002 | Bestetti et al. |
| 5,913,847 A | 6/1999 | Yoon | | 6,413,458 B1 | 7/2002 | Pearce |
| 5,916,198 A | 6/1999 | Dillow | | 6,420,475 B1 | 7/2002 | Chen |
| 5,916,232 A | 6/1999 | Hart | | 6,423,036 B1 | 7/2002 | Van Huizen |
| 5,919,476 A | 7/1999 | Fischer et al. | | 6,440,061 B1 | 8/2002 | Wenner et al. |
| 5,931,832 A | 8/1999 | Jensen | | 6,440,063 B1 | 8/2002 | Beane et al. |
| 5,947,922 A | 9/1999 | MacLeod | | 6,443,957 B1 | 9/2002 | Addis |
| 5,951,467 A | 9/1999 | Picha et al. | | 6,447,489 B1 | 9/2002 | Peterson |
| 5,951,588 A | 9/1999 | Moenning | | 6,450,983 B1 | 9/2002 | Rambo |
| 5,957,888 A | 9/1999 | Hinchiffe et al. | | 6,454,783 B1 | 9/2002 | Piskun |

| | | | | | | |
|---|---|---|---|---|---|---|
| 6,464,686 | B1 | 10/2002 | O'Hara et al. | 7,033,319 | B2 | 4/2006 | Pulford et al. |
| 6,468,292 | B1 | 10/2002 | Mollenauer et al. | 7,052,454 | B2 | 5/2006 | Taylor |
| 6,482,181 | B1 | 11/2002 | Racenet et al. | 7,056,304 | B2 | 6/2006 | Bacher et al. |
| 6,485,435 | B1 | 11/2002 | Bakal | 7,056,321 | B2 | 6/2006 | Pagliuca et al. |
| 6,485,467 | B1 | 11/2002 | Crook et al. | 7,067,583 | B2 | 6/2006 | Chen |
| 6,488,620 | B1 | 12/2002 | Segermark et al. | 7,077,852 | B2 | 7/2006 | Fogarty et al. |
| 6,488,692 | B1 | 12/2002 | Spence et al. | 7,081,089 | B2 | 7/2006 | Bonadio et al. |
| 6,494,893 | B2 | 12/2002 | Dubrul et al. | 7,083,626 | B2 | 8/2006 | Hart et al. |
| 6,527,787 | B1 | 3/2003 | Fogarty et al. | 7,093,599 | B2 | 8/2006 | Chen |
| 6,533,734 | B1 | 3/2003 | Corley, III et al. | 7,100,614 | B2 | 9/2006 | Stevens et al. |
| 6,551,270 | B1 | 4/2003 | Bimbo et al. | 7,101,353 | B2 | 9/2006 | Lui et al. |
| 6,551,276 | B1 | 4/2003 | Mann et al. | 7,105,009 | B2 | 9/2006 | Johnson |
| 6,551,344 | B2 | 4/2003 | Thill | 7,105,607 | B2 | 9/2006 | Chen |
| 6,552,109 | B1 | 4/2003 | Chen | 7,112,185 | B2 | 9/2006 | Hart et al. |
| 6,554,793 | B1 | 4/2003 | Pauker et al. | 7,118,528 | B1 | 10/2006 | Piskun |
| 6,558,371 | B2 | 5/2003 | Dorn | 7,134,929 | B2 | 11/2006 | Chen |
| 6,569,120 | B1 | 5/2003 | Green | 7,153,261 | B2 | 12/2006 | Wenchell |
| 6,578,577 | B2 | 6/2003 | Bonadio et al. | 7,163,510 | B2 | 1/2007 | Kahle et al. |
| 6,579,281 | B2 | 6/2003 | Palmer et al. | 7,192,436 | B2 | 3/2007 | Sing et al. |
| 6,582,364 | B2 | 6/2003 | Butler et al. | 7,193,002 | B2 | 3/2007 | Chen |
| 6,589,167 | B1 | 7/2003 | Shimomura et al. | 7,195,590 | B2 | 3/2007 | Butler et al. |
| 6,589,211 | B1 | 7/2003 | MacLeod | 7,214,185 | B1 | 5/2007 | Rosney et al. |
| 6,607,504 | B2 | 8/2003 | Haarala et al. | 7,217,277 | B2 | 5/2007 | Parihar et al. |
| 6,613,952 | B2 | 9/2003 | Rambo | 7,222,380 | B2 | 5/2007 | Chen |
| 6,623,426 | B2 | 9/2003 | Bonadio et al. | 7,223,257 | B2 | 5/2007 | Shubayev et al. |
| 6,627,275 | B1 | 9/2003 | Chen | 7,223,278 | B2 | 5/2007 | Davison et al. |
| 6,663,598 | B1 | 12/2003 | Carrillo et al. | 7,226,484 | B2 | 6/2007 | Chen |
| 6,669,674 | B1 | 12/2003 | Macoviak et al. | 7,235,062 | B2 | 6/2007 | Brustad |
| 6,676,639 | B1 | 1/2004 | Ternström | 7,235,084 | B2 | 6/2007 | Skakoon et al. |
| 6,702,787 | B2 | 3/2004 | Racenet et al. | 7,238,154 | B2 | 7/2007 | Ewers et al. |
| 6,705,989 | B2 | 3/2004 | Cuschieri et al. | 7,244,244 | B2 | 7/2007 | Racenet et al. |
| 6,706,050 | B1 | 3/2004 | Giannadakis | 7,276,075 | B1 | 10/2007 | Callas et al. |
| 6,714,298 | B2 | 3/2004 | Ryer | 7,290,367 | B2 | 11/2007 | Chen |
| 6,716,201 | B2 | 4/2004 | Blanco | 7,294,103 | B2 | 11/2007 | Bertolero et al. |
| 6,723,044 | B2 | 4/2004 | Pulford et al. | 7,297,106 | B2 | 11/2007 | Yamada et al. |
| 6,723,088 | B2 | 4/2004 | Gaskill, III et al. | 7,300,399 | B2 | 11/2007 | Bonadio et al. |
| 6,725,080 | B2 | 4/2004 | Melkent et al. | 7,316,699 | B2 | 1/2008 | McFarlane |
| 6,793,621 | B2 | 9/2004 | Butler et al. | 7,331,940 | B2 | 2/2008 | Sommerich |
| 6,794,440 | B2 | 9/2004 | Chen | 7,338,473 | B2 | 3/2008 | Campbell et al. |
| 6,796,940 | B2 | 9/2004 | Bonadio et al. | 7,344,546 | B2 | 3/2008 | Piskun |
| 6,797,765 | B2 | 9/2004 | Pearce | 7,344,547 | B2 | 3/2008 | Piskun |
| 6,800,084 | B2 | 10/2004 | Davison et al. | 7,344,568 | B2 | 3/2008 | Chen |
| 6,811,546 | B1 | 11/2004 | Callas et al. | 7,377,898 | B2 | 5/2008 | Ewers et al. |
| 6,814,078 | B2 | 11/2004 | Crook | 7,390,317 | B2 | 6/2008 | Taylor et al. |
| 6,814,700 | B1 | 11/2004 | Mueller et al. | 7,393,322 | B2 | 7/2008 | Wenchell |
| 6,817,974 | B2 | 11/2004 | Cooper et al. | 7,412,977 | B2 | 8/2008 | Fields et al. |
| 6,830,578 | B2 | 12/2004 | O'Heeron et al. | 7,445,597 | B2 | 11/2008 | Butler et al. |
| 6,837,893 | B2 | 1/2005 | Miller | 7,473,221 | B2 | 1/2009 | Ewers et al. |
| 6,840,946 | B2 | 1/2005 | Fogarty et al. | 7,481,765 | B2 | 1/2009 | Ewers et al. |
| 6,840,951 | B2 | 1/2005 | de la Torre et al. | 7,537,564 | B2 | 5/2009 | Bonadio et al. |
| 6,846,287 | B2 | 1/2005 | Bonadio et al. | 7,540,839 | B2 | 6/2009 | Butler et al. |
| 6,860,463 | B2 | 3/2005 | Hartley | 7,559,893 | B2 | 7/2009 | Bonadio et al. |
| 6,863,674 | B2 | 3/2005 | Kasahara et al. | 7,578,832 | B2 | 8/2009 | Johnson |
| 6,866,861 | B1 | 3/2005 | Luhman | 7,645,232 | B2 | 1/2010 | Shluzas |
| 6,867,253 | B1 | 3/2005 | Chen | 7,650,887 | B2 | 1/2010 | Nguyen et al. |
| 6,869,393 | B2 | 3/2005 | Butler | 7,661,164 | B2 | 2/2010 | Chen |
| 6,878,110 | B2 | 4/2005 | Yang et al. | 7,704,207 | B2 | 4/2010 | Albrecht et al. |
| 6,884,253 | B1 | 4/2005 | McFarlane | 7,717,847 | B2 | 5/2010 | Smith |
| 6,890,295 | B2 | 5/2005 | Michels et al. | 7,727,146 | B2 | 6/2010 | Albrecht et al. |
| 6,895,965 | B2 | 5/2005 | Scarberry et al. | 7,727,225 | B2 | 6/2010 | Taylor et al. |
| 6,902,541 | B2 | 6/2005 | McNally et al. | 7,736,306 | B2 | 6/2010 | Brustad et al. |
| 6,902,569 | B2 | 6/2005 | Parmer et al. | 7,749,415 | B2 | 7/2010 | Brustad et al. |
| 6,908,430 | B2 | 6/2005 | Caldwell et al. | 7,753,901 | B2 | 7/2010 | Piskun et al. |
| 6,909,220 | B2 | 6/2005 | Chen | 7,758,500 | B2 | 7/2010 | Boyd et al. |
| 6,913,609 | B2 | 7/2005 | Yencho et al. | 7,766,824 | B2 | 8/2010 | Jensen et al. |
| 6,916,310 | B2 | 7/2005 | Sommerich | 7,811,251 | B2 | 10/2010 | Wenchell et al. |
| 6,916,331 | B2 | 7/2005 | Mollenauer et al. | 7,815,567 | B2 | 10/2010 | Albrecht et al. |
| 6,929,637 | B2 | 8/2005 | Gonzalez et al. | 7,837,612 | B2 | 11/2010 | Gill et al. |
| 6,936,037 | B2 | 8/2005 | Bubb et al. | 7,850,667 | B2 | 12/2010 | Gresham |
| 6,939,296 | B2 | 9/2005 | Ewers et al. | 7,867,164 | B2 | 1/2011 | Butler et al. |
| 6,945,932 | B1 | 9/2005 | Caldwell et al. | 7,878,974 | B2 | 2/2011 | Brustad et al. |
| 6,958,037 | B2 | 10/2005 | Ewers et al. | 7,896,889 | B2 | 3/2011 | Mazzocchi et al. |
| 6,972,026 | B1 | 12/2005 | Caldwell et al. | 7,909,760 | B2 | 3/2011 | Albrecht et al. |
| 6,979,324 | B2 | 12/2005 | Bybordi et al. | 7,930,782 | B2 | 4/2011 | Chen |
| 6,991,602 | B2 | 1/2006 | Nakazawa et al. | 2001/0037053 | A1 | 11/2001 | Bonadio et al. |
| 6,997,909 | B2 | 2/2006 | Goldberg | 2001/0047188 | A1 | 11/2001 | Bonadio et al. |
| 7,001,397 | B2 | 2/2006 | Davison et al. | 2002/0002324 | A1 | 1/2002 | McManus |
| 7,008,377 | B2 | 3/2006 | Beane et al. | 2002/0010389 | A1 | 1/2002 | Butler et al. |
| 7,014,628 | B2 | 3/2006 | Bousquet | 2002/0013542 | A1 | 1/2002 | Bonadio et al. |

| | | | | | | |
|---|---|---|---|---|---|---|
| 2002/0016607 A1 | 2/2002 | Bonadio et al. | | 2006/0047293 A1 | 3/2006 | Haberland et al. |
| 2002/0026230 A1 | 2/2002 | Moll et al. | | 2006/0052669 A1 | 3/2006 | Hart |
| 2002/0038077 A1 | 3/2002 | de la Torre et al. | | 2006/0084842 A1 | 4/2006 | Hart et al. |
| 2002/0072762 A1 | 6/2002 | Bonadio et al. | | 2006/0106402 A1 | 5/2006 | McLucas |
| 2002/0111536 A1 | 8/2002 | Cuschieri et al. | | 2006/0129165 A1 | 6/2006 | Edoga et al. |
| 2003/0004253 A1 | 1/2003 | Chen | | 2006/0149137 A1 | 7/2006 | Pingleton et al. |
| 2003/0014076 A1 | 1/2003 | Mollenauer et al. | | 2006/0149306 A1 | 7/2006 | Hart et al. |
| 2003/0028179 A1 | 2/2003 | Piskun | | 2006/0161049 A1 | 7/2006 | Beane et al. |
| 2003/0040711 A1 | 2/2003 | Racenet et al. | | 2006/0161050 A1 | 7/2006 | Butler et al. |
| 2003/0078478 A1 | 4/2003 | Bonadio et al. | | 2006/0241651 A1 | 10/2006 | Wilk |
| 2003/0139756 A1 | 7/2003 | Brustad | | 2006/0247498 A1 | 11/2006 | Bonadio et al. |
| 2003/0167040 A1 | 9/2003 | Bacher et al. | | 2006/0247499 A1 | 11/2006 | Butler et al. |
| 2003/0187376 A1 | 10/2003 | Rambo | | 2006/0247500 A1 | 11/2006 | Voegele et al. |
| 2003/0192553 A1 | 10/2003 | Rambo | | 2006/0247516 A1 | 11/2006 | Hess et al. |
| 2003/0225392 A1 | 12/2003 | McMichael et al. | | 2006/0247586 A1 | 11/2006 | Voegele et al. |
| 2003/0236505 A1 | 12/2003 | Bonadio et al. | | 2006/0247673 A1 | 11/2006 | Voegele et al. |
| 2003/0236549 A1 | 12/2003 | Bonadio et al. | | 2006/0247678 A1 | 11/2006 | Weisenburgh, II et al. |
| 2004/0015185 A1 | 1/2004 | Ewers et al. | | 2006/0258899 A1 | 11/2006 | Gill et al. |
| 2004/0024363 A1 | 2/2004 | Goldberg | | 2006/0264706 A1 | 11/2006 | Piskun |
| 2004/0049099 A1 | 3/2004 | Ewers et al. | | 2006/0270911 A1 | 11/2006 | Voegele et al. |
| 2004/0049100 A1 | 3/2004 | Butler | | 2007/0004968 A1 | 1/2007 | Bonadio et al. |
| 2004/0054353 A1 | 3/2004 | Taylor | | 2007/0049966 A1 | 3/2007 | Bonadio et al. |
| 2004/0063833 A1 | 4/2004 | Chen | | 2007/0088202 A1 | 4/2007 | Albrecht et al. |
| 2004/0068232 A1 | 4/2004 | Hart et al. | | 2007/0088204 A1 | 4/2007 | Albrecht et al. |
| 2004/0070187 A1 | 4/2004 | Chen | | 2007/0093695 A1 | 4/2007 | Bonadio et al. |
| 2004/0072942 A1 | 4/2004 | Chen | | 2007/0118175 A1 | 5/2007 | Butler et al. |
| 2004/0073090 A1 | 4/2004 | Butler | | 2007/0149859 A1 | 6/2007 | Albrecht et al. |
| 2004/0092795 A1 | 5/2004 | Bonadio et al. | | 2007/0151566 A1 | 7/2007 | Kahle et al. |
| 2004/0092796 A1 | 5/2004 | Butler et al. | | 2007/0156023 A1 | 7/2007 | Frasier et al. |
| 2004/0093018 A1 | 5/2004 | Johnson | | 2007/0185387 A1 | 8/2007 | Albrecht et al. |
| 2004/0097793 A1 | 5/2004 | Butler et al. | | 2007/0203398 A1 | 8/2007 | Bonadio et al. |
| 2004/0106942 A1 | 6/2004 | Taylor | | 2007/0208312 A1 | 9/2007 | Norton et al. |
| 2004/0111061 A1 | 6/2004 | Curran | | 2007/0255219 A1 | 11/2007 | Vaugh et al. |
| 2004/0127772 A1 | 7/2004 | Ewers et al. | | 2007/0299387 A1 | 12/2007 | Williams et al. |
| 2004/0138529 A1 | 7/2004 | Wiltshire et al. | | 2008/0027476 A1 | 1/2008 | Piskun |
| 2004/0143158 A1 | 7/2004 | Hart et al. | | 2008/0048011 A1 | 2/2008 | Weller |
| 2004/0154624 A1 | 8/2004 | Bonadio et al. | | 2008/0097162 A1 | 4/2008 | Bonadio et al. |
| 2004/0167559 A1 | 8/2004 | Taylor et al. | | 2008/0097163 A1 | 4/2008 | Butler et al. |
| 2004/0173218 A1 | 9/2004 | Yamada et al. | | 2008/0200767 A1 | 8/2008 | Ewers et al. |
| 2004/0215063 A1 | 10/2004 | Bonadio et al. | | 2008/0255519 A1 | 10/2008 | Piskun et al. |
| 2004/0230161 A1 | 11/2004 | Zeiner | | 2008/0281161 A1 | 11/2008 | Albrecht et al. |
| 2004/0243144 A1 | 12/2004 | Bonadio et al. | | 2008/0281162 A1 | 11/2008 | Albrecht et al. |
| 2004/0249248 A1 | 12/2004 | Bonadio et al. | | 2009/0012477 A1 | 1/2009 | Norton et al. |
| 2004/0254426 A1 | 12/2004 | Wenchell | | 2009/0036745 A1 | 2/2009 | Bonadio et al. |
| 2004/0260244 A1 | 12/2004 | Piechowicz et al. | | 2009/0069837 A1 | 3/2009 | Bonadio et al. |
| 2004/0267096 A1 | 12/2004 | Caldwell et al. | | 2009/0093683 A1 | 4/2009 | Richard et al. |
| 2005/0020884 A1 | 1/2005 | Hart et al. | | 2009/0093752 A1 | 4/2009 | Richard et al. |
| 2005/0033246 A1 | 2/2005 | Ahlbert et al. | | 2009/0131754 A1 | 5/2009 | Ewers et al. |
| 2005/0059865 A1 | 3/2005 | Kahle et al. | | 2009/0137879 A1 | 5/2009 | Ewers et al. |
| 2005/0065475 A1 | 3/2005 | Hart et al. | | 2009/0149714 A1 | 6/2009 | Bonadio |
| 2005/0065543 A1 | 3/2005 | Kahle et al. | | 2009/0182279 A1 | 7/2009 | Wenchell et al. |
| 2005/0090713 A1 | 4/2005 | Gonzales et al. | | 2009/0187079 A1 | 7/2009 | Albrecht et al. |
| 2005/0090716 A1 | 4/2005 | Bonadio et al. | | 2009/0227843 A1 | 9/2009 | Smith et al. |
| 2005/0090717 A1 | 4/2005 | Bonadio et al. | | 2009/0292176 A1 | 11/2009 | Bonadio et al. |
| 2005/0096695 A1 | 5/2005 | Olich | | 2009/0326330 A1 | 12/2009 | Bonadio et al. |
| 2005/0131349 A1 | 6/2005 | Albrecht et al. | | 2010/0063362 A1 | 3/2010 | Bonadio et al. |
| 2005/0148823 A1 | 7/2005 | Vaugh et al. | | 2010/0063364 A1 | 3/2010 | Bonadio et al. |
| 2005/0155611 A1 | 7/2005 | Vaugh et al. | | 2010/0081880 A1 | 4/2010 | Widenhouse et al. |
| 2005/0159647 A1 | 7/2005 | Hart et al. | | 2010/0081881 A1 | 4/2010 | Murray et al. |
| 2005/0192483 A1 | 9/2005 | Bonadio et al. | | 2010/0081995 A1 | 4/2010 | Widenhouse et al. |
| 2005/0192598 A1 | 9/2005 | Johnson et al. | | 2010/0100043 A1 | 4/2010 | Racenet |
| 2005/0197537 A1 | 9/2005 | Bonadio et al. | | 2010/0113882 A1 | 5/2010 | Widenhouse et al. |
| 2005/0203346 A1 | 9/2005 | Bonadio et al. | | 2010/0217087 A1 | 8/2010 | Bonadio et al. |
| 2005/0209510 A1 | 9/2005 | Bonadio et al. | | 2010/0228091 A1 | 9/2010 | Widenhouse et al. |
| 2005/0222582 A1 | 10/2005 | Wenchell | | 2010/0228092 A1 | 9/2010 | Ortiz et al. |
| 2005/0240082 A1 | 10/2005 | Bonadio et al. | | 2010/0228094 A1 | 9/2010 | Ortiz et al. |
| 2005/0241647 A1 | 11/2005 | Nguyen | | 2010/0240960 A1 | 9/2010 | Richard |
| 2005/0251124 A1 | 11/2005 | Zvuloni et al. | | 2010/0249523 A1 | 9/2010 | Spiegel et al. |
| 2005/0261720 A1 | 11/2005 | Caldwell et al. | | 2010/0249524 A1 | 9/2010 | Ransden et al. |
| 2005/0267419 A1 | 12/2005 | Smith | | 2010/0249525 A1 | 9/2010 | Shelton, IV et al. |
| 2005/0277946 A1 | 12/2005 | Greenhalgh | | 2010/0249694 A1 | 9/2010 | Choi et al. |
| 2005/0283050 A1 | 12/2005 | Gundlapalli et al. | | 2010/0261972 A1 | 10/2010 | Widenhouse et al. |
| 2005/0288558 A1 | 12/2005 | Ewers et al. | | 2010/0261975 A1 | 10/2010 | Huey et al. |
| 2005/0288634 A1 | 12/2005 | O'Heeron et al. | | 2010/0286484 A1 | 11/2010 | Stellon et al. |
| 2006/0020164 A1 | 1/2006 | Butler et al. | | 2010/0298646 A1 | 11/2010 | Stellon et al. |
| 2006/0020241 A1 | 1/2006 | Piskun et al. | | 2011/0021877 A1 | 1/2011 | Fortier et al. |
| 2006/0030755 A1 | 2/2006 | Ewers et al. | | 2011/0028891 A1 | 2/2011 | Okoniewski |
| 2006/0041270 A1 | 2/2006 | Lenker | | 2011/0034935 A1 | 2/2011 | Kleyman |
| 2006/0047284 A1 | 3/2006 | Gresham | | 2011/0034946 A1 | 2/2011 | Kleyman |

| | | | |
|---|---|---|---|
| 2011/0034947 A1 | 2/2011 | Kleyman | |
| 2011/0071462 A1 | 3/2011 | Ewers et al. | |
| 2011/0071463 A1 | 3/2011 | Ewers et al. | |

FOREIGN PATENT DOCUMENTS

| | | |
|---|---|---|
| DE | 33 36 279 C2 | 1/1986 |
| DE | 37 39 532 | 12/1988 |
| DE | 37 37 121 | 5/1989 |
| DE | 296 00 939 | 6/1996 |
| DE | 19828009 | 12/1999 |
| EP | 0113520 | 7/1984 |
| EP | 0142262 | 5/1985 |
| EP | 0 517 248 | 12/1992 |
| EP | 0537768 | 4/1993 |
| EP | 0 807 416 | 11/1997 |
| EP | 0 849 517 | 6/1998 |
| EP | 0950376 | 10/1999 |
| EP | 1118657 | 7/2001 |
| EP | 1 125 552 | 8/2001 |
| EP | 1312318 | 5/2003 |
| EP | 1 407 715 | 4/2004 |
| EP | 2044889 | 4/2009 |
| FR | 1456623 | 9/1966 |
| GB | 1151993 | 5/1969 |
| GB | 1355611 | 6/1974 |
| GB | 1372491 | 10/1974 |
| GB | 1379772 | 1/1975 |
| GB | 1400808 | 7/1975 |
| GB | 1407023 | 9/1975 |
| GB | 1482857 | 8/1977 |
| GB | 1496696 | 12/1977 |
| GB | 2071502 | 9/1981 |
| GB | 2255019 | 10/1992 |
| GB | 2275420 | 8/1994 |
| GB | 2298906 | 9/1996 |
| IE | 930649 | 9/1993 |
| IE | 930650 | 9/1993 |
| IE | S940150 | 2/1994 |
| IE | S940613 | 8/1994 |
| IE | S940960 | 12/1994 |
| IE | S950055 | 1/1995 |
| IE | S950266 | 4/1995 |
| IE | S75368 | 8/1997 |
| IE | S960196 | 8/1997 |
| IE | S970810 | 11/1997 |
| IE | 991010 | 7/2000 |
| IE | 990218 | 11/2000 |
| IE | 990219 | 11/2000 |
| IE | 990220 | 11/2000 |
| IE | 990660 | 2/2001 |
| IE | 990795 | 3/2001 |
| JP | 10-108868 | 4/1998 |
| JP | 11-290327 | 10/1999 |
| JP | 2001-61850 | 3/2001 |
| JP | 2002-28163 | 1/2002 |
| JP | 02003 235879 A | 8/2003 |
| JP | 2004-195037 | 7/2004 |
| SU | 1342485 | 1/1997 |
| WO | WO 86/06272 | 11/1986 |
| WO | WO 86/06316 | 11/1986 |
| WO | WO 92/11880 | 7/1992 |
| WO | WO 92/21292 | 12/1992 |
| WO | WO 93/05740 | 4/1993 |
| WO | WO 93/14801 | 8/1993 |
| WO | WO 94/04067 | 3/1994 |
| WO | WO 94/22357 | 10/1994 |
| WO | WO 95/05207 | 2/1995 |
| WO | WO 95/07056 | 3/1995 |
| WO | WO 95/22289 | 8/1995 |
| WO | WO 95/24864 | 9/1995 |
| WO | WO 95/27445 | 10/1995 |
| WO | WO 95/27468 | 10/1995 |
| WO | WO 96/36283 | 11/1996 |
| WO | WO 97/11642 | 4/1997 |
| WO | WO 97/32514 | 9/1997 |
| WO | WO 97/32515 | 9/1997 |
| WO | WO 97/42889 | 11/1997 |
| WO | WO 98/19853 | 5/1998 |
| WO | WO 98/35614 | 8/1998 |
| WO | WO 98/48724 | 11/1998 |
| WO | WO 99/03416 | 1/1999 |
| WO | WO 99/15068 | 4/1999 |
| WO | WO 99/16368 | 4/1999 |
| WO | WO 99/22804 | 5/1999 |
| WO | WO 99/25268 | 5/1999 |
| WO | WO 99/29250 | 6/1999 |
| WO | WO 00/32116 | 6/2000 |
| WO | WO 00/32119 | 6/2000 |
| WO | WO 00/32120 | 6/2000 |
| WO | WO 00/35356 | 6/2000 |
| WO | WO 00/54675 | 9/2000 |
| WO | WO 00/54676 | 9/2000 |
| WO | WO 00/54677 | 9/2000 |
| WO | WO 01/08563 | 2/2001 |
| WO | WO 01/08581 | 2/2001 |
| WO | WO 01/26558 | 4/2001 |
| WO | WO 01/26559 | 4/2001 |
| WO | WO 01/45568 | 6/2001 |
| WO | WO 01/49363 | 7/2001 |
| WO | WO 01/91652 | 12/2001 |
| WO | WO 02/07611 | 1/2002 |
| WO | WO 02/17800 | 3/2002 |
| WO | WO 02/34108 | 5/2002 |
| WO | WO 03/011153 | 2/2003 |
| WO | WO 03/011551 | 2/2003 |
| WO | WO 03/026512 | 4/2003 |
| WO | WO 03/032819 | 4/2003 |
| WO | WO 03/034908 | 5/2003 |
| WO | WO 03/061480 | 7/2003 |
| WO | WO 03/077726 | 9/2003 |
| WO | WO 03/103548 | 12/2003 |
| WO | WO 2004/026153 | 4/2004 |
| WO | WO 2004/030547 | 4/2004 |
| WO | WO 2004/075730 | 9/2004 |
| WO | WO 2004/075741 | 9/2004 |
| WO | WO 2004/075930 | 9/2004 |
| WO | WO 2005/009257 | 2/2005 |
| WO | WO 2005/034766 | 4/2005 |
| WO | WO 2005/089661 | 9/2005 |
| WO | WO 2006/040748 | 4/2006 |
| WO | WO 2006/059318 | 6/2006 |
| WO | WO 2006/100658 | 9/2006 |
| WO | WO 2008/015566 | 2/2008 |
| WO | WO 2008/093313 | 8/2008 |
| WO | WO 2008/121294 | 10/2008 |
| WO | WO 2010/082722 | 7/2010 |
| WO | WO 2010/104259 | 9/2010 |

OTHER PUBLICATIONS

The International Bureau of WIPO, International Preliminary Report on Patentability for International Applicaltion No. PCT/US2008/063463, dated Nov. 17, 2009, entitled "Surgical Retractor".

European Patent Office, European Search Report for European Patent No. 11172709.5, dated Aug. 16, 2011.

European Patent Office, European Search Report for European Patent No. 11172706.1, dated Aug. 16, 2011.

U.S. Appl. No. 10/381,220, filed Mar. 20, 2003; Title: Surgical Access Apparatus and Method, now USPN 7,473,221 issued Jan. 6, 2009.

U.S. Appl. No. 10/436,522, filed May 13, 2003; Title: Laparoscopic Illumination Apparatus and Method, now USPN 6,939,296 issued Sep. 6, 2005.

U.S. Appl. No. 10/399,209, filed Aug. 22, 2003; Title: Wound Retraction Apparatus and Method, now USPN 6,958,037 issued Oct. 25, 2005.

U.S. Appl. No. 11/218,412, filed Sep. 1, 2005; Title: Wound Retraction Apparatus and Method, now USPN 7,238,154 issued Jul. 3, 2007.

U.S. Appl. No. 10/399,057, filed Apr. 11, 2003; Title: Sealed Surgical Access Device, now USPN 7,052,454 issued May 30, 2006.

U.S. Appl. No. 10/666,579, filed Sep. 17, 2003; Title: Surgical Instrument Access Device, now USPN 7,163,510 issued Jan. 16, 2007.

U.S. Appl. No. 10/052,297, filed Jan. 18, 2002; Title: Hand Access Port Device, now USPN 6,908,430 issued Jun. 21, 2005.

U.S. Appl. No. 08/015,765, filed Feb. 10, 1993; Title: Gas-Tight Seal Accomodating Surgical Instruments With a Wide Range of Diameters, now USPN 5,407,433 issued Apr. 18, 1995.
U.S. Appl. No. 08/040,373, filed Mar. 30, 1993; Title: Gas-Tight Seal Accomodating Surgical Instruments With a Wide Range of Diameters, now USPN 5,411,483 issued May 2, 1995.
U.S. Appl. No. 10/902,756, filed Jul. 29, 2004; Title: Hand Access Port Device, now abandoned.
U.S. Appl. No. 10/802,125, filed Mar. 15, 2004; Title: Surgical Guide Valve, now abandoned.
U.S. Appl. No. 10/516,198, filed Nov. 30, 2004; Title: Wound Retractor, now USPN 7,650,887 issued Jan. 26, 2010.
U.S. Appl. No. 10/927,551, filed Aug. 25, 2004; Title: Surgical Access System, now abandoned.
U.S. Appl. No. 11/244,647, filed Oct. 5, 2005; Title: Surgical Access Apparatus and Method, now USPN 7,481,765 issued Jan. 27, 2009.
U.S. Appl. No. 11/548,746, filed Oct. 12, 2006; Title: Method of Making a Hand Access Laparoscopic Device, now USPN 7,749,415 issued Jul. 6, 2010.
U.S. Appl. No. 11/548,765, filed Oct. 12, 2006; Title: Split Hoop Wound Retractor, now USPN 7,815,567 issued Oct. 26, 2010.
U.S. Appl. No. 11/548,767, filed Oct. 12, 2006; Title: Circular Surgical Retractor now USPN 7,704,207 issued Apr. 27, 2010.
U.S. Appl. No. 11/548,781, filed Oct. 12, 2006; Title: Wound Retractor With Gel Cap, now USPN 7,727,146 issued Jun. 1, 2010.
U.S. Appl. No. 11/548,955, filed Oct. 12, 2006; Title: Hand Access Laparoscopic Device, now USPN 7,736,306 issued Jun. 15, 2010.
U.S. Appl. No. 11/755,305, filed May 30, 2007; Title: Wound Retraction Apparatus and Method, now USPN 7,377,898 issued May 27, 2008.
U.S. Appl. No. 11/548,758, filed Oct. 12, 2007; Title: Split Hoop Wound Retractor With Gel Pad, now USPN 7,909,760 issued Mar. 22, 2011.
U.S. Appl. No. 12/693,242, filed Jan. 1, 2010; Title: Wound Retractor, now USPN 7,913,697 issued Mar. 29, 2011.
U.S. Appl. No. 12/768,328, filed Apr. 27, 2010; Title: Circular Surgical Retractor, now USPN 7,892,172 issued Feb. 22, 2011.
U.S. Appl. No. 12/791,666, filed Jun. 1, 2010; Title: Wound Retractor With Gel Cap, now USPN 7,883,461 issued Feb. 8, 2011.
U.S. Appl. No. 12/815,986, filed Jun. 15, 2010; Title: Hand Access Laparoscopic Device, now USPN 7,878,974 issued Feb. 1, 2011.
U.S. Appl. No. 10/695,295, filed Oct. 28, 2003; Title: Surgical Gel Seal.
U.S. Appl. No. 11/132,741, filed May 18, 2005; Title: Gas-Tight Seal Accomodating Surgical Instruments With a Wide Range of Diameters.
U.S. Appl. No. 11/245,709, filed Oct. 7, 2005; Title: Surgical Access System.
U.S. Appl. No. 11/330,661, filed Jan. 12, 2006; Title: Sealed Surgical Access Device.
U.S. Appl. No. 11/564,409, filed Nov. 29, 2006; Title: Surgical Instrument Access Device.
U.S. Appl. No. 12/108,400, filed Apr. 23, 2008; Title: Wound Retraction Apparatus and Method.
U.S. Appl. No. 12/119,371, filed May 12, 2008; Title: Surgical Retractor With Gel Pad.
U.S. Appl. No. 12/119,414, filed May 12, 2008; Title: Surgical Retractor.
U.S. Appl. No. 12/358,080, filed Jan. 22, 2009; Title: Surgical Instrument Access Device.
U.S. Appl. No. 12/360,634, filed Jan. 27, 2009; Title: Surgical Access Apparatus and Method.
U.S. Appl. No. 12/360,710, filed Jan. 27, 2009; Title: Surgical Access Apparatus and Method.
U.S. Appl. No. 12/578,422, filed Oct. 13, 2009; Title: Single Port Access System.
U.S. Appl. No. 12/905,932, filed Oct. 15, 2010; Title: Split Hoop Wound Retractor.
U.S. Appl. No. 12/960,449, filed Dec. 3, 2010; Title: Surgical Access Apparatus and Method.
U.S. Appl. No. 12/960,458, filed Dec. 3, 2010; Title: Surgical Access Apparatus and Method.
U.S. Appl. No. 13/006,727, filed Jan. 14, 2011.
U.S. Appl. No. 13/008,728, filed Jan. 18, 2011.
U.S. Appl. No. 13/023,334, filed Feb. 8, 2011.
U.S. Appl. No. 13/031,892, filed Feb. 22, 2011.
U.S. Appl. No. 13/050,042, filed Mar. 17, 2011.
U.S. Appl. No. 10/446,365, filed May 28, 2003; Title: Screw-Type Seal With Inflatable Membrane.
U.S. Appl. No. 12/004,439, filed Dec. 20, 2007; Title: Skin Seal.
U.S. Appl. No. 12/004,441, filed Dec. 20, 2007; Title: Screw-Type Skin Seal With Inflatable Membrane.
U.S. Appl. No. 12/607,667, filed Oct. 28, 2009; Title: Screw-Type Skin Seal With Inflatable Membrane.
U.S. Appl. No. 10/965,217, filed Oct. 15, 2004; Title: Surgical Sealing Device.
U.S. Appl. No. 10/981,730, filed Nov. 5, 2004; Title: Surgical Sealing Device.
U.S. Appl. No. 11/246,909, filed Oct. 11, 2005; Title: Instrument Access Device.
U.S. Appl. No. 11/291,089, filed Dec. 1, 2005; Title: A Surgical Sealing Device.
U.S. Appl. No. 11/486,383, filed Jul. 14, 2006; Title: Wound Retractor.
U.S. Appl. No. 11/785,752, filed Apr. 19, 2007; Title: Instrument Access Device.
U.S. Appl. No. 12/244,024, filed Oct. 2, 2008; Title: Seal Anchor for Use in Surgical Procedures.
U.S. Appl. No. 12/578,832, filed Oct. 14, 2009; Title: Flexible Access Device for Use in Surgical Procedure.
U.S. Appl. No. 12/706,043, filed Feb. 16, 2010; Title: Flexible Port Seal.
U.S. Appl. No. 12/719,341, filed Mar. 8, 2010; Title: Foam Port and Introducer Assembly.
U.S. Appl. No. 10/895,546, filed Jul. 21, 2004; Title: Laparoscopic Instrument and Cannula Assembly and Related Surgical Method.
U.S. Appl. No. 10/913,565, filed Aug. 5, 2004; Title: Surgical Device With Tack-Free Gel and Method of Manufacture.
Dexterity Protractor Instruction Manual by Dexterity Surgical, Inc., 1999.
European Patent Office, European Search Report for European Application No. EP 10 18 4681, dated Nov. 22, 2010, entitled "Wound Retraction Apparatus and Method".
European Patent Office, European Search Report for European Application No. EP 10 18 4608, dated Nov. 22, 2010, entitled "Wound Retraction Apparatus and Method".
European Patent Office, European Search Report for European Application No. EP 10 18 4648, dated Nov. 22, 2010, entitled "Wound Retraction Apparatus and Method".
European Patent Office, European Search Report for European Application No. EP 10 18 4731, dated Nov. 22, 2010, entitled "Wound Retraction Apparatus and Method".
European Patent Office, European Search Report for European Application No. EP 10 18 4661, dated Nov. 22, 2010, entitled "Wound Retraction Apparatus and Method".
European Patent Office, European Search Report for European Application No. EP 10 18 4677, dated Nov. 22, 2010, entitled "Wound Retraction Apparatus and Method".
European Patent Office, European Search Report for European Application No. EP 10 18 9325, dated Dec. 14, 2010, entitled "Split Hoop Wound Retractor".
European Patent Office, European Search Report for European Application No. EP 10 18 9327, dated Dec. 14, 2010, entitled "Split Hoop Wound Retractor".
European Patent Office, European Search Report for European Application No. EP 10 18 9328, dated Dec. 15, 2010, entitled "Split Hoop Wound Retractor".
European Patent Office, European Search Report for European Application No. EP 04 00 2888, dated Sep. 10, 2004, entitled "Hand Access Port Device".
European Patent Office, European Search Report for European Application No. EP 04 00 2889, dated Sep. 13, 2004, entitled "Hand Access Port Device".
European Patent Office, International Search Report and the Written Opinion of the International Searching Authority for International Application No. PCT/US2006/040154, mailed Jan. 30, 2007.

European Patent Office, International Search Report and the Written Opinion of the International Searching Authority for International Application No. PCT/US2006/040073, mailed Jan. 26, 2007.

European Patent Office, International Search Report and the Written Opinion of the International Searching Authority for International Application No. PCT/US2006/039905, mailed Jan. 17, 2007.

European Patent Office, International Search Report and the Written Opinion of the International Searching Authority for International Application No. PCT/US2006/039883, mailed Jan. 31, 2007.

European Patent Office, International Search Report and the Written Opinion of the International Searching Authority for International Application No. PCT/US2006/039800, mailed Apr. 16, 2007.

European Patent Office, International Search Report and the Written Opinion of the International Searching Authority for International Application No. PCT/US2006/039799, mailed Mar. 27, 2007.

European Search Report for corresponding EP 08253236 date of mailing is Feb. 10, 2009 (6 pages).

Horigame, et al., Silicone Rumen Cannula with a Soft Cylindrical Part and a Hard Flange, Journal of Dairy Science, Nov. 1989, vol. 72, No. 11, pp. 3230-3232.

Horigame, et al., Technical Note: Development of Duodoenal Cannula for Sheep, Journal of Animal Science, Apr. 1992, vol. 70, Issue 4, pp. 1216-1219.

International Searching Authority/US, International Search Report and the Written Opinion of the International Searching Authority for International Application No. PCT/US04/05484, Nov. 12, 2004.

International Searching Authority/US, International Search Report and the Written Opinion of the International Searching Authority for International Application No. PCT/US01/29682, Jun. 14, 2002.

McSweeney, Cannulation of the Rumen in Cattle and Buffaloes, Australian Veterniary Journal, Aug. 1989, vol. 66, No. 8, pp. 266-268.

Neil Sheehan, Supplemental Expert Report of Neil Sheehan, Re: U.S. Patent No. 5,741,298, United States District Court for the Central District of California, Civil Action No. SACV 03-1322 JVS, Aug. 9, 2005.

Office Action in co-pending U.S. Appl. No. 12/360,634, dated Jan. 24, 2011 in 12 pages.

Office Action in co-pending U.S. Appl. No. 12/360,710, dated Jan. 24, 2011 in 12 pages.

Technical Note: Development of Duodenal Cannula for Sheep, Faculty of Agriculture and School of Medicine Tohokju University, Sendai 981, Japan.

The International Bureau of WIPO, International Preliminary Report on Patentability, dated Aug. 29, 2006, for International Application No. PCT/US2004/028250.

The International Bureau of WIPO, International Preliminary Report on Patentability, dated Apr. 16, 2008, for International Application No. PCT/US2006/039799.

The International Bureau of WIPO, International Preliminary Report on Patentability for International Application No. PCT/US2006/039800 dated Apr. 16, 2008.

Yamazaki, et al., Diurnal Changes in the Composition of Abomasal Digesta in Fasted and Fed Sheep, The Tohoki Journal of Agricultural Research, Mar. 1987, vol. 37, No. 3-4, pp. 49-58.

Kagaya, Laparascopic cholecystecomy via two ports, using the "Twin-Port" system, J. Hepatobiliary Pancreat Surg (2001) 8:76-80.

International Search Report and Written Opinion in PCT/IE2005/000113 mailed on Feb. 22, 2006.

International Search Report and Written Opinion in PCT/IE2007/000050 mailed on Aug. 13, 2007.

Declaration of John R. Brustad dated Dec. 10, 2009, submitted in U.S. Appl. No. 11/548,955, including Appendices A-D regarding product sales brochures and production drawings from 2001 and 2005.

The International Searching Authority, The International Search Report and Written Opinion of the International Searching Authority for International Application No. PCT/US08/063463 mailed Sep. 10, 2008.

The International Bureau of WIPO, International Preliminary Report on Patentability for International Application No. PCT/US2008/063463, dated Nov. 17, 2009, entitled "Surgical Retractor".

The International Bureau of WIPO, International Preliminary Report on Patentability for International Application No. PCT/US08/63445, issued Nov. 17, 2009, entitled "Surgical Retractor with Gel Pad".

International Searching Authority-US, International Search Report and Written Opinion of the International Searching Authority for International Application No. PCT/US04/25511, mailed Nov. 7, 2007.

International Bureau of WIPO, International Report on Patentability for International Application No. PCT/US04/25511, mailed Dec. 6, 2007.

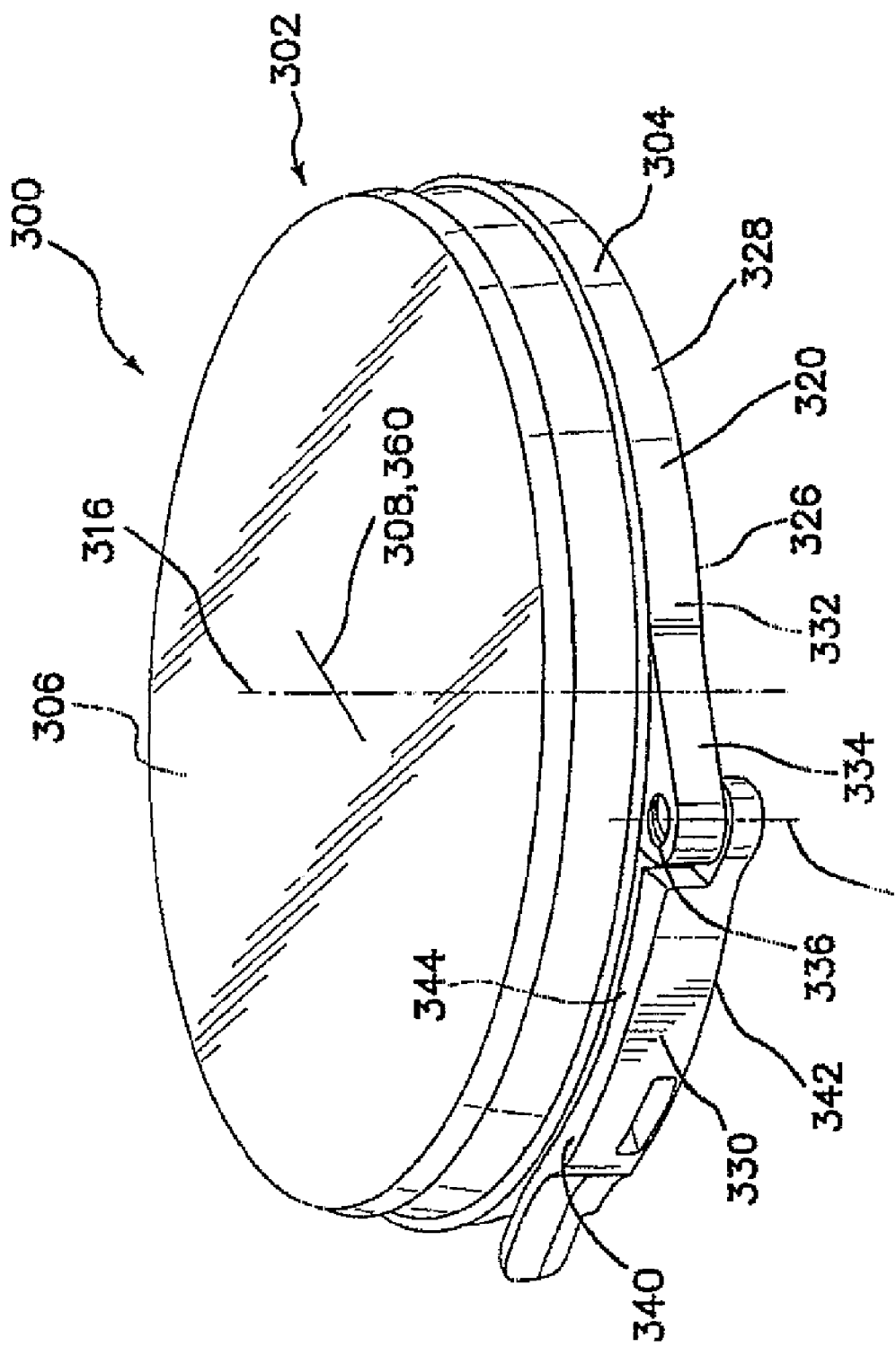

SURGICAL RETRACTOR

CROSS-REFERENCE TO RELATED APPLICATIONS

This application claims the benefits of and priority to U.S. Provisional Patent Application No. 60/917,571, filed on May 11, 2007, the disclosure of which is hereby incorporated by reference as if set forth in full herein.

BACKGROUND

The present invention relates generally to surgical tissue retractors and specifically to retractors that may be used to enlarge a surgical incision or a natural body opening. Retraction of a surgical incision or body opening is generally accomplished by placing a first, flexible retention member through the incision or body opening and into a body cavity, such as an abdominal cavity, and subsequently tensioning the first retention member against the inner portion of the associated body wall adjacent to the incision or opening by applying tension to a sleeve that is coupled to the first tension member. The sleeve may be tensioned by winding it upon an external, more rigid structure. As the sleeve is wound around the external structure, the incision or opening is reshaped and/or enlarged to a substantially round condition.

SUMMARY

The invention relates generally to a surgical retractor for retracting a surgical incision or a natural biological body orifice. A surgical retractor has a noncompliant outer ring, an inner ring, and a sleeve that couples the outer ring to the inner ring. The outer ring has an annular axis and is adapted for juxtaposition with an outer surface of the biological body wall. The inner ring is adapted for juxtaposition with an inner surface of the biological body wall. The sleeve is adapted to traverse the opening in the body wall. The noncompliant outer ring is adapted to roll over itself around the annular axis to roll the sleeve around the outer ring in order to retract and seal the opening in the body wall. The noncompliant outer ring is adapted to have a lid coupled to it. The outer ring of the surgical retractor has a cross-sectional shape that prohibits the lid from being partially or incorrectly coupled to the outer ring of the surgical retractor.

In one aspect, the outer ring of the surgical retractor has an oval cross-sectional shape. The outer ring of the surgical retractor has a first, outer portion that has at least one lumen, and a second, inner portion that has a noncompliant hoop. The noncompliant hoop is positioned in the at least one lumen of the first, outer portion. In one aspect, the at least one lumen in the first, outer portion of the outer ring has a first, middle lumen, a second, top lumen, and a third, bottom lumen, with the noncompliant hoop of the second, inner portion of the outer ring being positioned in the first, middle lumen. The first, outer portion of the outer ring may have the oval cross-sectional shape with the first, second, and third lumens of the first, outer portion of the outer ring being positioned along a major axis of the oval cross-section. The first lumen is positioned at a minor axis of the oval cross-section, the second lumen is positioned on a first side of the minor axis and the third lumen is positioned on a second, opposite side of the minor axis. A split hoop may be positioned in each of the second and third lumens of the first, outer portion of the outer ring. In one aspect, the first, outer portion of the outer ring of the surgical retractor has two lumens with a noncompliant split hoop positioned in each of the two lumens. The first, outer portion of the outer ring is made of materials that allow the outer ring to be turned around its annular axis. The sleeve is made of a material that is flexible and impermeable to fluids and bacteria. The inner ring is made of materials having sufficient hardness to retain the shape of the inner ring after insertion of the inner ring into a body cavity.

These and other features and advantages of the invention will become more apparent with a discussion of embodiments in reference to the associated drawings.

BRIEF DESCRIPTION OF THE DRAWINGS

FIG. 10 is a perspective view of a gel cap for use with a surgical retractor in accordance with various aspects of the present invention.

DESCRIPTION

Figure 1A:
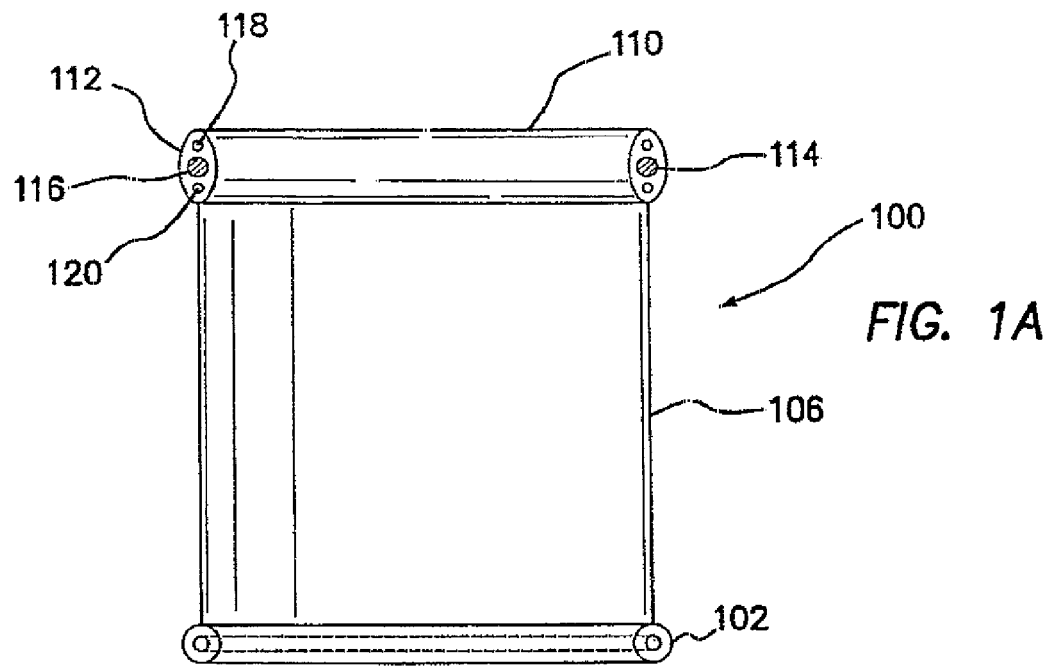
FIG. 1A is a side view of a surgical retractor in accordance with various aspects of the present invention.
Figure 1B:
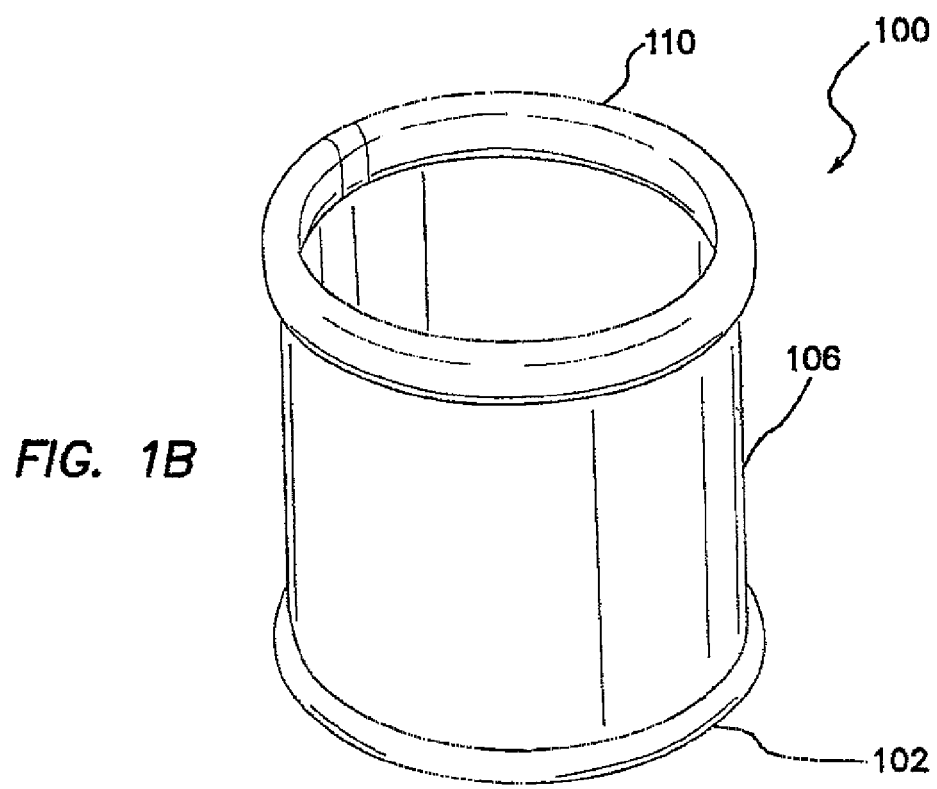
FIG. 1B is a perspective view of a surgical retractor in accordance with various aspects of the present invention.
Figure 2A:
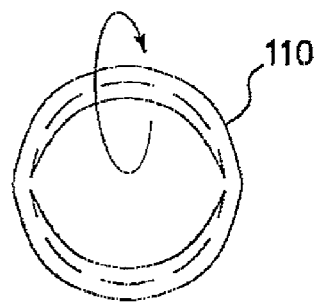
FIGS. 2A-2C are views of an outer ring of a surgical retractor in accordance with various aspects of the present invention.
Figure 2B:
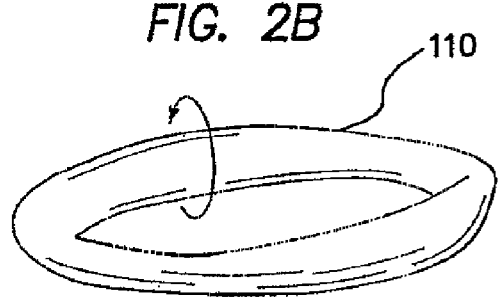
Figure 2C:

A surgical wound retractor 100 is placed into a surgical incision or body orifice to enlarge, reshape and isolate the incision or body orifice. Referring to FIGS. 1 and 2, the surgical retractor 100 includes a first, inner ring 102, a second, outer ring 110 and a sleeve 106 that couples the inner ring to the outer ring. The sleeve is flexible and may be substantially cylindrical. The first, inner ring 102 may be sufficiently flexible to be shaped into a compressed condition for insertion into the incision or body orifice and subsequently released within an associated body cavity where the inner ring substantially regains its original shape. In one aspect, the first, inner ring includes a substantially circular shape when it is released. The first, inner ring may be compressed to a substantially oval shape for insertion through the incision or body orifice. Those with ordinary skill in the art will recognize that the first, inner ring may include a shape other than round and that it may be compressed and reshaped to a shape other than oval. Once the first, inner ring is properly deployed within a body cavity, the connecting sleeve or film may be tensioned to some appropriate degree between the first, inner ring and the second, outer ring.

The second, outer ring 110 includes a first, outer component 112 and a second, inner component 114. The first, outer component 112 includes an overall shape that is substantially circular and may include a substantially oval cross-section. In one aspect, the height of the cross-section of the first, outer component 112 is larger than the width of the cross-section. The ratio between the height and width of the cross-section relates to the hardness of the first, outer component 112 material and the diameter of the second, outer ring 110. More particularly, with a softer material for the first, outer component 112, the ratio between the height and width of the cross-section of the first, outer component is greater. Similarly, with the first, outer component 112 having a greater diameter, the ratio between the height and width of the cross-section of the first, outer component is greater. The first, outer component 112 may be made of a thermoplastic elastomeric material, such as a HYTREL, a thermoplastic polyester elastomeric material manufactured by E.I. DuPont de Nemours & Co of Wilmington, Del., and/or PELLETHANE, a thermoplastic polyurethane elastomeric material manufactured by The Dow Chemical Company of Midland, Mich.

In one aspect, the first, outer component 112 of the second, outer ring 110 includes three lumens that extend throughout the outer component. A first, middle lumen 116 may include an oval cross-section and be sized larger than a second, top lumen 118 and a third, bottom lumen 120. The second, top lumen 118 and third, bottom lumen 120 may each include a tear-dropped cross-section having tapered portions away from the first, middle lumen 116. The first 116, second 118, and third 120 lumens are positioned substantially along a major axis of the oval cross-section of the outer component 112. The first lumen 116 is further positioned substantially at a minor axis of the oval cross-section of the outer component 112 of the outer ring 110, the second lumen 118 is positioned on a first side of the minor axis and the third lumen 120 is positioned on a second, opposite side of the minor axis. Alternatively, the lumens may include other cross-sectional shapes, such as round.

The first, outer component 112 of the second, outer ring 110 may be made of a split piece of material, such as a substantially straight piece of material, having a first end 122 and a second end 124. The first 122 and second 124 ends of the material forming the first, outer component 112 may be brought proximate each other and coupled together, as will be discussed in more detail below.

In one aspect, the second, inner component 114 of the outer ring 110 is made of a rigid wire that is bent into a generally circular shape. The second, inner component 114 is inserted into the first, middle lumen 116 of the first, outer component 112. The wire is not compliant or resilient in relation to the body tissue of the surgical incision or natural body orifice. The wire does not flex, yield or deform in relation to the body tissue of the surgical incision or natural body orifice during retraction of the incision or body orifice. The rigid wire dictates the peripheral shape, or footprint, of the second, outer ring of the surgical retractor. The rigid wire marks the center point of rotation for the second, outer ring 110, thereby functioning as an axle about which the first, outer component 112 rotates. The wire may be made of full hard stainless steel, or other material that is significantly harder than the first, outer component 112 of the second, outer ring 110. The wire of which the second, inner component 114 is made may be a split wire having a first 126 end and a second end 128. In one aspect, the first 126 and second 128 ends of the rigid wire are coupled together.

Figure 3:
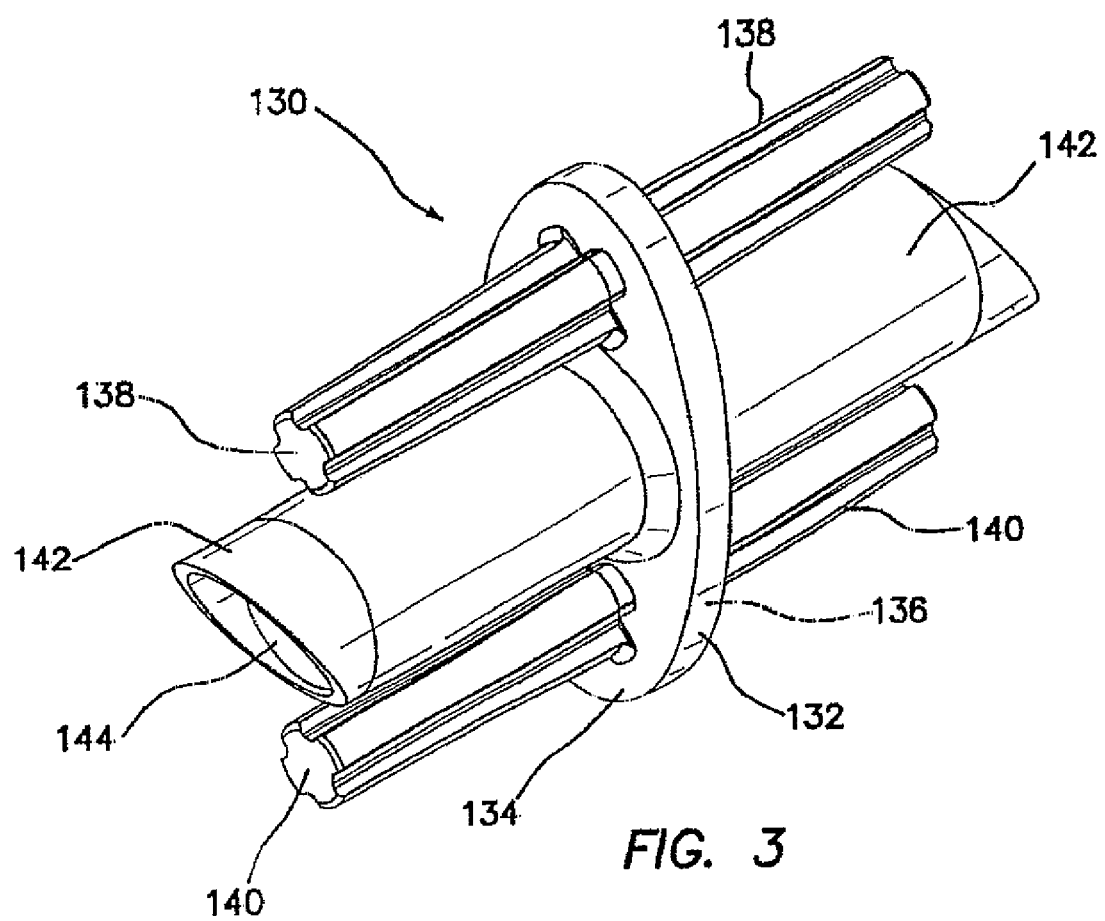
FIG. 3 is a perspective view of a coupler for the outer ring of the surgical retractor in accordance with various aspects of the present invention.
Figure 4:
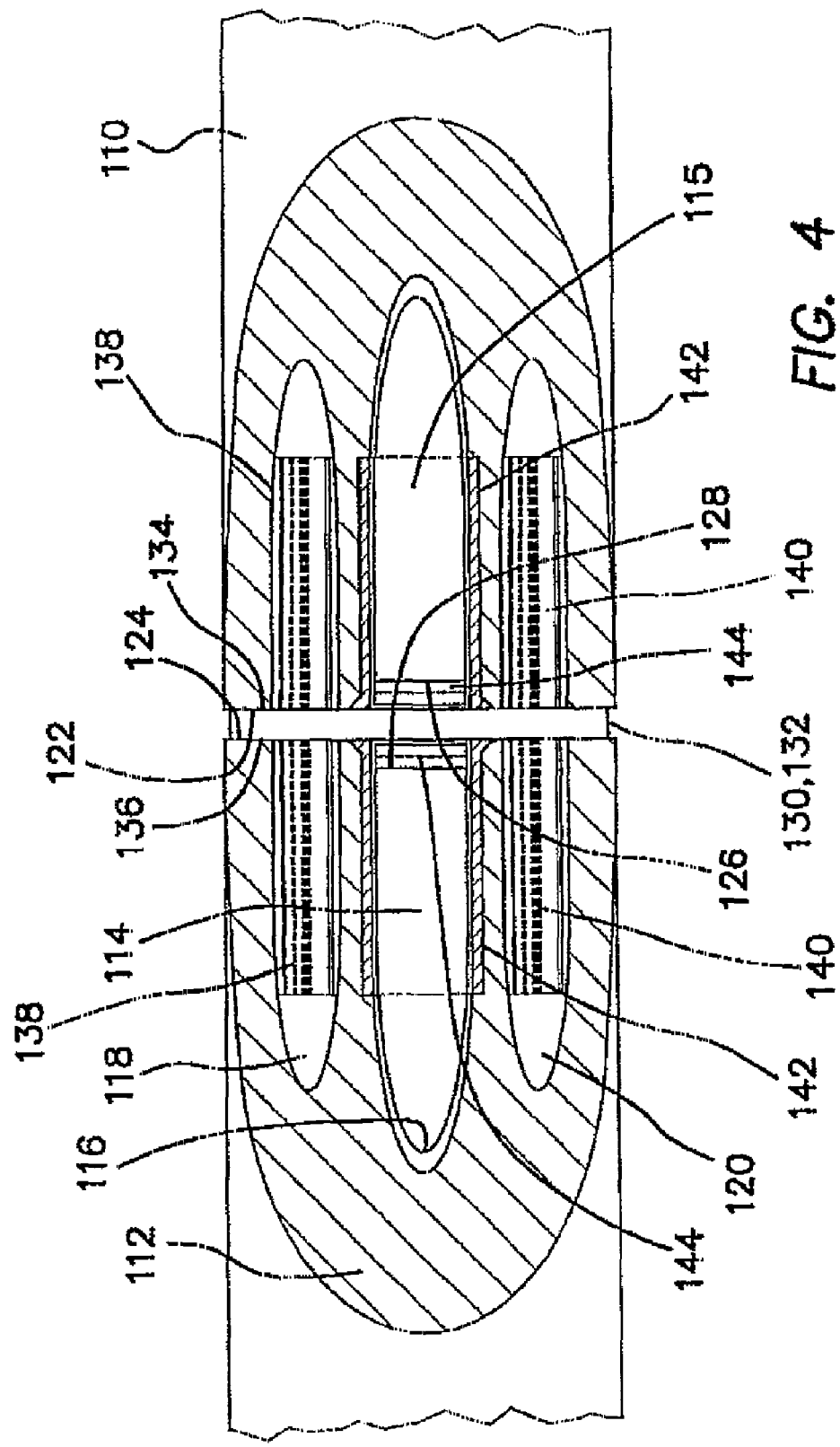
FIG. 4 is a side view of an outer ring of a surgical retractor, partially in cross section, in accordance with various aspects of the present invention.

Referring to FIGS. 3 and 4, in one aspect the second outer ring 110 includes a single monolithic coupler 130 for coupling the first 122 and second 124 ends of the first, outer component 112 of the outer ring together and to couple the first 126 and second 128 ends of the second, inner component 114 of the outer ring together. The single monolithic coupler 130 may be made of plastic or other suitable material. In one aspect, the monolithic coupler may be made of Acrylonitrile Butadiene Styrene (ABS), high density polyethylene (HDPE) or HYTREL.

The monolithic coupler includes a base portion 132 having a first face 134, a second face 136 opposing the first face, and a periphery that substantially matches the periphery of the cross-section of the first, outer component 112 of the second, outer ring 110. Each of the first 134 and second 136 faces of the base portion 132 of the monolithic coupler 130 has a first pin 138, a second pin 140 and a tube portion 142 protruding therefrom with the pins and tube portion on each face being substantially symmetrical to the pins and tube portion on the opposing face. The first 138 and second 140 pins on the first face 134 of the monolithic coupler base 132 are positioned, aligned and adapted to mate with the second 118 and third 120 lumens, respectively, at the first end 122 of the first, outer component 112 of the second, outer ring 110. Similarly, the first 138 and second 140 pins on the second face 136 of the monolithic coupler base 132 are positioned, aligned and adapted to mate with the second 118 and third lumens 120, respectively, at the second end 124 of the first, outer component 112 of the second, outer ring 110. The tube portion 142 on the first face 134 of the monolithic coupler base 132 is aligned and adapted to mate with the first lumen 116 at the first end 122 of the first, outer component 112 of the second, outer ring 110 and the tube portion 142 on the second face 136 of the monolithic coupler base 132 is aligned and adapted to mate with the first lumen 116 at the second end 124 of the first, outer component 112 of the second, outer ring 110. Each of the tube portions 142 of the monolithic coupler 130 includes an aperture 144 that is open at the end of the tube portion away from the base 132 of the monolithic coupler. Alternatively, the monolithic coupler 130 may include an aperture 144 that extends completely through the tube portion 142 on the first face 134, the base portion 132, and the tube portion 142 on the second face 136. The aperture 144 of each of the tube portions 142 of the monolithic coupler 130 is adapted to receive one of the first 126 and second 128 ends of the rigid ring 115 of the second, inner component 114 of the second, outer ring 110 of the surgical retractor 100.

The first 138 and second 140 pins on each of the first 134 and second 136 faces of the monolithic coupler base 132 tapers away from the base. The taper on the pins facilitates insertion of the pins into the respective lumens 118, 120 of the first, outer component 112 of the second, outer ring 110. The outer surface of the tube portions 142 on each of the first 134 and second 136 faces of the monolithic coupler base 132 also tapers away from the base with the taper facilitating insertion of the tube portions into the first lumen 116 of the first, outer component 112 of the second, outer ring 110. The aperture 144 of each of the tube portions 142 is tapered toward the monolithic coupler base 132 to facilitate the insertion of one of the first 126 and second 128 ends of the second, inner component 114 of the second, outer ring 110 therein.

The length of each of the tube portions 142 of the monolithic coupler 130 is sufficient to maintain the first 126 and second 128 ends of the second, inner component 114 of the second, outer ring 110 therein and to maintain the tube portions within the first, middle lumen 116 of the first, outer component 112 of the second, outer ring. Similarly, the first 138 and second 140 pins protruding from the first 134 and second 136 faces of the monolithic coupler base 132 are of sufficient length to maintain the pins in the second 118 and third 120 lumens, respectively, of the first, outer component 112 of the second, outer ring 110. Being made of Acrylonitrile Butadiene Styrene (ABS), the monolithic coupler 130 is flexible and the pins 138, 140 and tube portions 142 thereof may assume a curved shape as influenced upon by the rigid wire 115 of the second, inner component 114 of the second, outer ring 110 and by the first, outer component 112 of the second, outer ring. Alternatively, the monolithic coupler 130 may be substantially rigid and may be made by methods including die casting, metal injection molding, and/or powdered metallurgy.

The first, inner ring 102 may include a single component having an overall substantially circular shape and a substantially circular cross-section. The first, inner ring 102 may be made of a material that is softer than the material of which the first, outer component 112 of the second, outer ring 110 is made. Alternatively, the first, inner ring 102 may be made of a material having about the same hardness as the material of which the first, outer component 112 of the second, outer ring 110 is made or may be made of a material that is harder than the material of which the first, outer component of the second, outer ring is made. The sleeve 106 may be made of a flexible, semi-transparent plastic film that is coupled to the first, inner ring 102 and the second, outer ring 110.

Referring again to the first, outer component 112 of the second, outer ring 110, the ratio of the cross-sectional height and width of the first, outer component creates lock points as the outer component is rotated about the second, inner component 112. As the sleeve 106 is rolled around the second, outer ring 110, while the outer ring is rotated, the lock points prevent the outer ring from rotating back, and thus prevent the sleeve from unraveling from the second, outer ring. The lock points also provide incremental rotational positions for the second, outer ring, thereby providing incremental retraction of the wound. Generally symmetrical cross-sectional shapes provide substantially uniform rotational motion and lock points, thereby providing a substantially uniform "snap" feel with each incremental rotation. The lock points also help keep the first, outer component of the second, outer ring from tilting as a result of forces encountered when retracting the surgical incision or body orifice.

The footprint of the second, outer ring 110 can be symmetrical or non-symmetrical and can vary in size and shape, such as a circle, ellipse or other suitable shape, to conform to a body type, position or size and thereby increase the working space or reduce potential interference with other instruments or ports during the laparoscopic procedure.

As stated above, the first, outer component 112 may be made of a thermoplastic elastomeric material, such as HYTREL or PELLETHANE. Increasing the hardness of the material used for the first, outer component increases resistance to lock the second, outer ring 110 in position with each rotation of the outer ring. The type of material used for the first, outer component can affect the height and width of the first, outer component to provide sufficient lock points for the second, outer ring. For example, the material hardness can be reduced while the height/width cross-section ratio of the first, outer component is increased. Conversely, the material hardness can be increased while the height/width cross-section ratio of the first, outer component is reduced. The first, outer component can be extruded, injection molded, compression molded, or over-molded. Those with ordinary skill in the art will recognize that other means for creating the first, outer component may be utilized. An over-molded first, outer component is substantially neutral, in relation to stress loads, and therefore experiences a difference in forces required to produce successive snaps. The difference in forces produced by an over-molded first, outer component may facilitate the outer component in maintaining a neutral position and in snapping or rotating into the neutral position. However, an over-molded first, outer component may also resist rotation of the outer component away from the neutral position. An extruded first, outer component may have the ends produced thereby heat sealed together.

The cross-sectional profile of the second, outer ring 110 of the surgical retractor 100 may be reduced to increase the insertion angle for instruments being inserted therethrough. More particularly, the cross-sectional height and/or width of the second, outer ring may be reduced. This is particularly useful for body orifice retraction, such as rectal or vaginal retraction. The more the profile of the second, outer ring is reduced, the more difficult it becomes to roll the first, outer component of the outer ring about the second, inner component of the outer ring and a tool may be required to facilitate rolling the outer component about the inner component.

Figure 9:
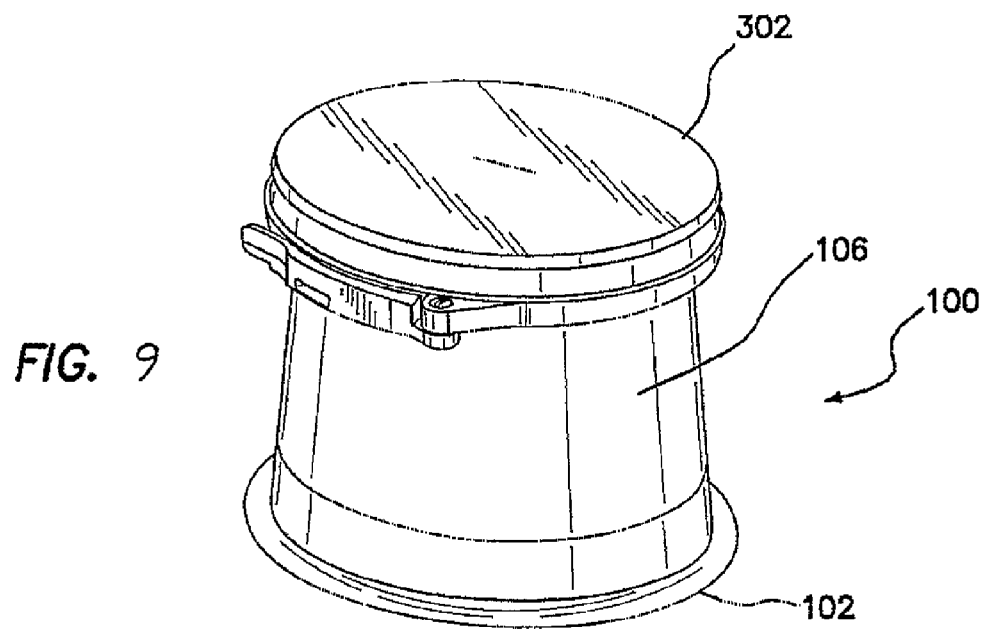
FIG. 9 is a perspective view of a surgical retractor with a gel cap in accordance with various aspects of the present invention.
Figure 11:
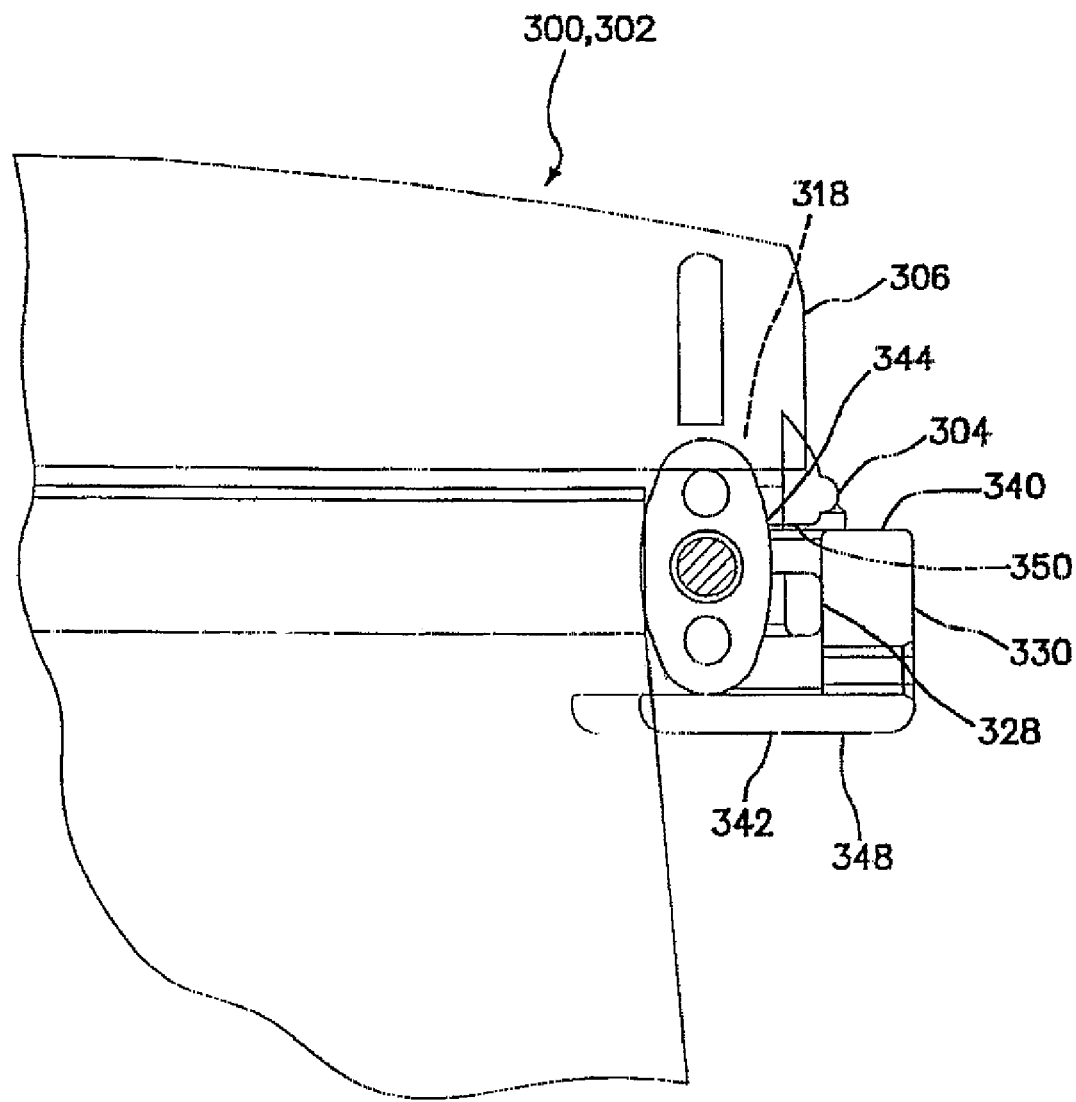
FIG. 11 is a side view, partially in cross section, of a surgical retractor and a gel cap in accordance with various aspects of the present invention.

Referring to FIGS. 9 and 11, a lid may be coupled to the outer ring 110 to maintain pneumoperitoneum. The lid may be removed to provide access into the body cavity 172. The lid may also be transparent so as to allow viewing into the body cavity without removal of the lid One such lid is a gel cap 300. The cross-sectional shape of the first, outer component 112 of the second, outer ring 110 of the surgical retractor 100 includes a shape that substantially prohibits the gel-cap 300 from being partially or incorrectly coupled to the second, outer ring of the surgical retractor. Such cross-sectional shapes include oval and rectangular, or other of numerous cross-sectional shapes that provide the same functionality.

As indicated above, the second, inner component 114 of the second, outer ring 110 may be made of a rigid wire 115 that is bent into a generally circular shape. The wire thickness for the rigid wire may be between about 0.25-12.70 mm (0.010-0.500 inches) in diameter. The wire thickness may vary in correlation to the wound or body opening size and the device size. For example, the larger the wound or body opening size is, the larger the wire size is. The wire diameter can also correlate to the wire material. For example, as the hardness of the material of the wire is increased, the wire diameter may be reduced.

The rigid wire 115 for the second, inner component 114 of the second, outer ring 110 may include a straight rigid wire. The straight rigid wire may be inserted into the first, middle lumen 116 of the first, outer component 112. When the ends 122, 124 of the first, outer component 112 of the second, outer ring 110 are joined, the wire 115 is forced to assume a substantially circular shape, placing the wire in a preloaded condition. The preloaded condition of the wire causes the wire to maintain a tendency to straighten out. The tendency of the wire to straighten out helps the second, outer ring 110 maintain a circular shape when the ends 122, 124 of the first, outer component 112 of the outer ring are joined.

Figure 5:
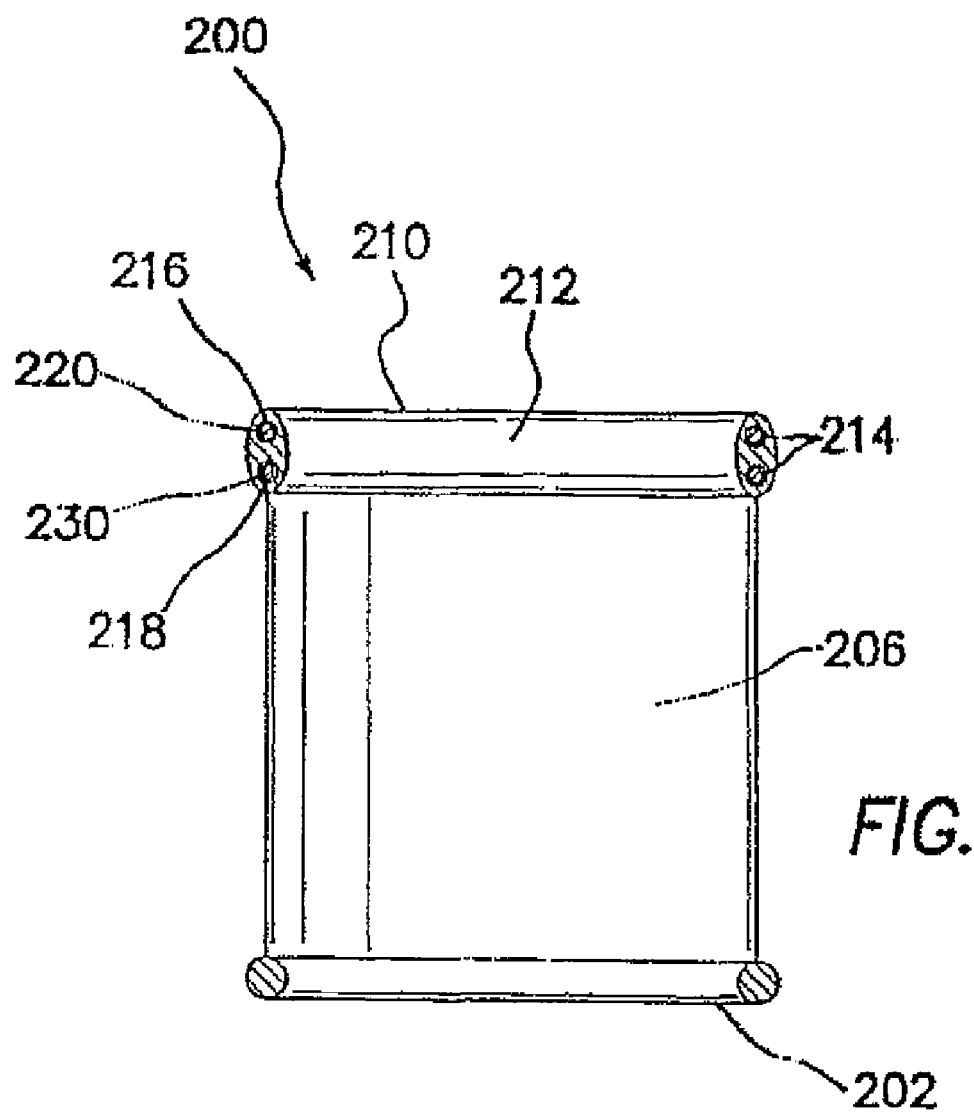
FIG. 5 is a side view of a surgical retractor, in cross section, in accordance with various aspects of the present invention.

Referring to FIG. 5, in one aspect, the second, outer ring 210 of the surgical retractor 200 includes a first, outer component 212 having a substantially oval cross-section including a first lumen 216 and a second lumen 218. Each of the first 216 and second 218 lumens is positioned substantially along the major axis of the oval with the first lumen positioned on a first side of the minor axis of the oval and the second lumen positioned on a second, opposite side of the minor axis of the oval. The second, inner component 214 of the second, outer ring 210 of the surgical retractor 200 includes a first substantially noncompliant, split hoop 220 positioned in the first lumen 216 of the first, outer component 212 of the outer ring and a second substantially noncompliant, split hoop 230 positioned in the second lumen of the outer component. Each of the first 220 and second 230 split hoops may include a hoop having a single split about its periphery with the split creating a first end of the split hoop and a second end of the split hoop. In its neutral position, the first and second ends of the respective split hoops substantially abut each other.

The first 220 and second 230 split hoops may be made of metals, such as stainless steel, piano wire heat treated to a spring temper, or other metals that produce a substantially noncompliant hoop. The first and second split hoops may also be formed of rigid polymeric materials through molding, machining, and other processes that are well known in the art. The substantially noncompliant split hoops may also be formed of other suitable rigid materials that are well known in the art.

The spacing between the first 216 and second 218 lumens of the first, outer component 212 of the second, outer ring 210 and the cross-sectional size of the first 220 and second 230 split hoops of the second, inner component 214 of the outer ring positioned within the first and second lumens dictates the effectiveness of the surgical retractor. During use, the second, outer ring of the surgical retractor 200 is rolled down by forcing one of the split hoops open, thereby causing a space between the first and second ends of the hoop, and around the other split hoop. In this manner, one of the rigid split hoops works as an axle or center of rotation for the other split hoop. By placing the two split hoops further apart or by increasing the strength of the split hoops, greater force is required to rotate the second, outer ring of the surgical retractor. The spacing between the first and second lumens and the cross-sectional size of the first and second split hoops may, therefore, be selected for a desired balance between the force required to rotate the second, outer ring against the tendency of the outer ring to unroll because of the force imparted on the outer ring by a retracted incision or body opening.

The cross-sectional diameter of the first 220 and second 230 split hoops may vary depending on the cross-section of the first outer component 212 of the second, outer ring 210 and on the size of the incision or body opening to be retracted. In one aspect, for incisions 5-9 cm in length, 3.0 mm diameter wire may be utilized. Each of the first and second hoops may be made of a wire having a thickness of about 0.25-6.35 mm (0.010-0.250 inches) in diameter.

The first 220 and second 230 split hoops of the second, inner component 214 of the second, outer ring 210 of the surgical retractor 200 may be formed of, for example, full-hard temper wire and to a peripheral size that is smaller than that which the first, outer component 212 of the outer ring would force the first and second split hoops into. In this manner, the first, outer component 212 of the second, outer ring 210 is held closed and the first 220 and second 230 split hoops control the orientation of the outer component during use. To attain a peripheral size of the first 220 and second 230 split hoops that is smaller than that which the first, outer component 212 of the second, outer ring 210 would force upon the first and second split hoops, the split hoops may be formed with first and second end portions of each of the split hoops overlapping each other. In one aspect, the materials of which the first, outer component 212 of the second, outer ring 210 is made, combined with the size of the first 216 and second 218 lumens of the outer component, do not permit the first and second end portions of the split hoops to overlap each other within the lumens. When the first 220 and second 230 split hoops are assembled with the first, outer component 212 of the second, outer ring 210, the overlap between the end portions of the first and second split hoops is removed and the first and second ends of each of the split hoops substantially abut each other with a spring force that causes the second, outer ring to remain closed. In this manner, the first 220 and second 230 split hoops facilitate stability of the second, outer ring 210 so that the cross-section of the first, outer component 212 remains vertical at 0° and 180° orientations, thereby facilitating the attachment of a cap 302 (FIG. 10) to the second, outer ring 210 of the surgical retractor 200. In one aspect, split hoops of varying cross-sectional size may be positioned within the first 216 and second 218 lumens of the first, outer component 212 of the second, outer ring 210 to create retractors that have a bias to determinable orientations.

Since each of the first 220 and second 230 split hoops has substantially abutting first and second ends, each of the split hoops functions as an axle about which the first, outer component 212 may turn for half a rotation, or 180°. More particularly, the second, outer ring 210 may be rolled such that the first split hoop 220 is rolled outside the second split hoop 230 with the periphery of the first split hoop expanding to clear the second split hoop. With continued rolling of the second, outer ring 210, the second split hoop 230 may be rolled outside the first split hoop 220 with the periphery of the second split hoop expanding to clear the first split hoop. These steps may be repeated until the incision or body opening is retracted to the desired degree.

The second, outer ring 210 of the surgical retractor 200 may be formed by transforming an extruded elastomeric tube into a circular ring by placing the first 220 and second 230 split hoops into the first 216 and second 218 lumens of the first, outer component 212 of the outer ring. This is accomplished by inserting one of the first and second ends of the first split hoop 220 into the first lumen 216 of the first, outer component 212 and inserting one of the first and second ends of the second split hoop 230 into the second lumen 218 of the first, outer component. Each of the first 220 and second 230 split hoops is continually fed into the respective lumen 216, 218 until each of the split hoops is substantially entirely within the respective lumen. The first, outer component 212 takes on the shape of the split hoops 220, 230 positioned in the first 216 and second 218 lumens thereof.

Figure 6:
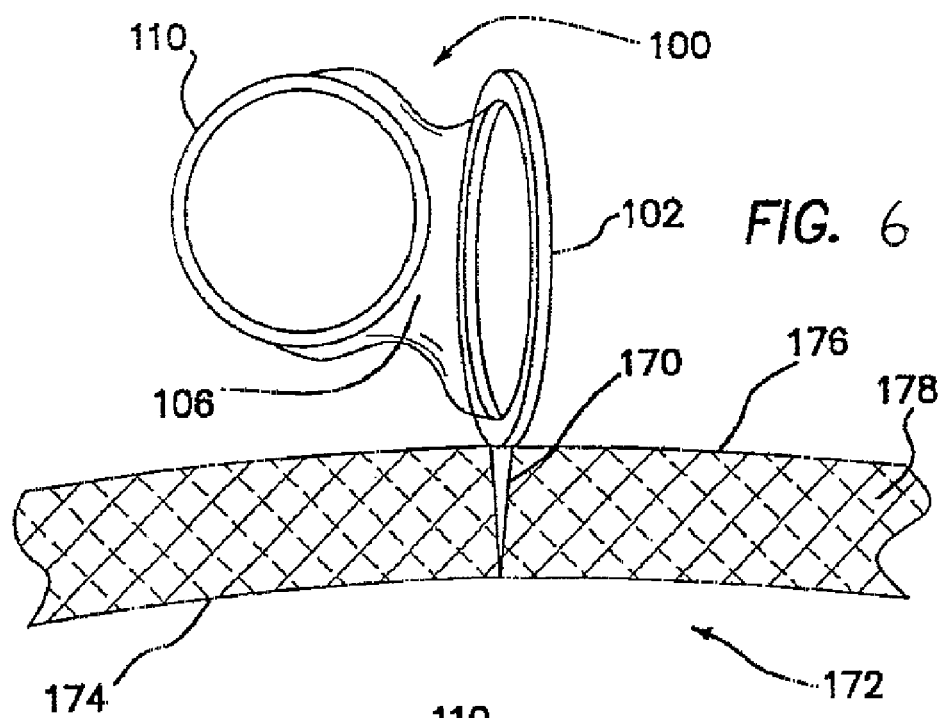
FIG. 6 is a side view of a surgical retractor in accordance with various aspects of the present invention being placed in a body wall.
Figure 7:
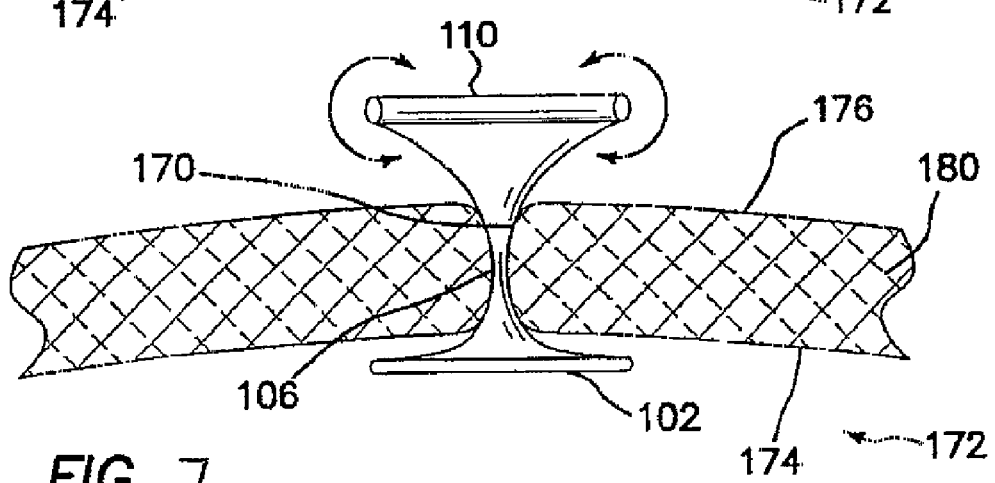
FIG. 7 is a side view of a surgical retractor in accordance with various aspects of the present invention being placed in a body wall.
Figure 8:
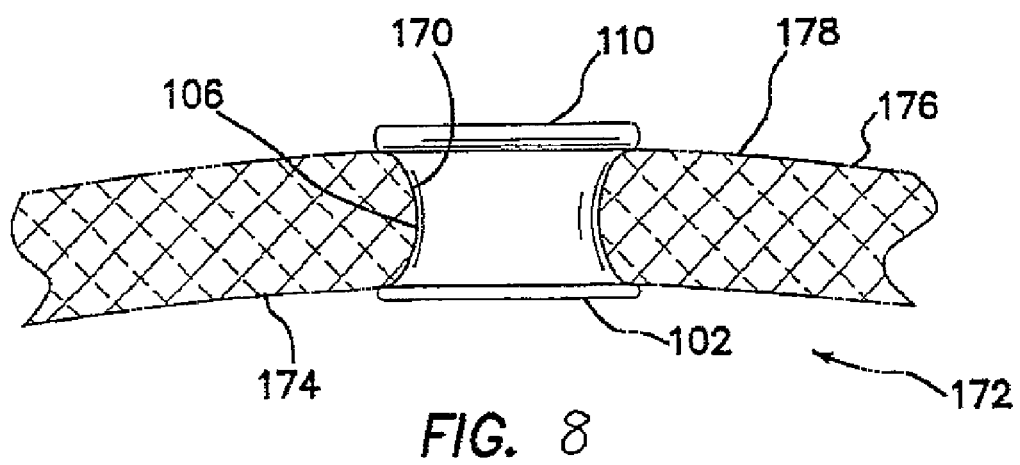
FIG. 8 is a side view of a surgical retractor in accordance with various aspects of the present invention being placed in a body wall.

Referring to FIGS. 6-8, in use a surgical retractor 100 is inserted into an incision 170 or body orifice by folding the first, inner ring 102 into an oval shape, or other shape, and urging it through the incision or body orifice. Once the first, inner ring 102 is fully within an associated body cavity 172, such as an abdominal cavity, it is allowed to resume an original, substantially circular condition, or other original shape, and pulled upward against the inner surface 174 of the body cavity. When the first, inner ring 102 is fully in place, the first, outer component 112 of the second, outer ring 110 is rolled about the second, inner component 114 of the outer ring, thereby rolling the sleeve 106 about the second, outer ring and tensioning the sleeve to retract the incision 170 or body orifice. The second, outer ring 110 is rolled until the outer ring, with the sleeve 106 wrapped around it, is substantially in contact with the exterior surface 176 of the body wall 178. When the second, outer ring 110 with the sleeve 106 wrapped around it is in contact with the exterior surface 176 of the body wall 178, the second, outer ring of the retractor is sufficiently rigid that it maintains the incision 170 or body opening substantially fully retracted. Moreover, when the second, outer ring 110 with the sleeve 106 wrapped around it is in contact with the exterior surface 176 of the body wall 178, the second, outer ring of the surgical retractor 100 is not flexible or likely to yield under the forces normally experienced during use of the surgical retractor. The rigid second, outer ring 110 facilitates the provision of 360° atraumatic retraction of the incision 170 or body opening. The surgical retractor 100 is a durable device that provides reliable protection of the incision 170 or body opening.

An advantage associated with the surgical access device is it enables a surgeon to quickly retract and protectively line an abdominal wall incision while being able to easily accommodate variations in abdominal wall thickness between patients. In addition, the device effectively seals around the interior and exterior of the incision, and allows a sealing cap to be coupled to the device to seal the abdominal cavity and to enable a laparoscopic procedure to be performed.

Many alterations and modifications may be made by those having ordinary skill in the art without departing from the spirit and scope of the invention. For these reasons, the above description should not be construed as limiting the invention, but should be interpreted as merely exemplary of the embodiments

The invention claimed is:

1. A surgical retractor for retracting an opening in a biological body wall, comprising,
    a substantially noncompliant outer ring having an annular axis and adapted for juxtaposition with an outer surface of the biological body wall;
    an inner ring adapted for juxtaposition with an inner surface of the biological body wall; and
    a sleeve coupling the outer ring to the inner ring, the sleeve being adapted to traverse the opening in the body wall,
    wherein the substantially noncompliant outer ring being adapted to roll over itself around the annular axis to roll the sleeve around the outer ring to retract and seal the opening in the body wall,
    wherein the substantially noncompliant outer ring comprises:
        a first, outer portion having at least one lumen; and
    wherein the at least one lumen of the first, outer portion of the outer ring of the surgical retractor has two lumens, and further comprises:
    a substantially noncompliant hoop positioned in each of the two lumens of the first, outer portion of the outer ring of the surgical retractor, each of the substantially noncompliant hoops having a split.

2. The surgical retractor of claim 1, the outer ring having an oval cross-sectional shape.

3. The surgical retractor of claim 1, the first, outer portion of the outer ring being made of materials that allow the outer ring to be turned around its annular axis.

4. The surgical retractor of claim 1, the sleeve comprising a material that is flexible and impermeable to fluids and bacteria.

5. The surgical retractor of claim 1, the inner ring being made of materials having sufficient hardness to retain the shape of the inner ring after insertion of the inner ring into a body cavity.

6. The surgical retractor of claim 1, wherein:
    the substantially noncompliant outer ring being adapted to receive a lid coupled thereto, and
    the outer ring having a cross-sectional shape that facilitates proper coupling of the lid to the outer ring.

7. A surgical retractor for retracting an opening in a biological body wall, comprising,
    a substantially noncompliant outer ring having an annular axis and adapted for juxtaposition with an outer surface of the biological body wall;
    an inner ring adapted for juxtaposition with an inner surface of the biological body wall; and
    a sleeve coupling the outer ring to the inner ring, the sleeve being adapted to traverse the opening in the body wall,
    wherein the substantially noncompliant outer ring being adapted to roll over itself around the annular axis to roll the sleeve around the outer ring to retract and seal the opening in the body wall,
    wherein the substantially noncompliant outer ring comprises:
        a first, outer portion having at least one lumen; and
    wherein the at least one lumen in the first, outer portion of the outer ring comprising:
        a first, middle lumen;
        a second, top lumen; and
        a third, bottom lumen,
    wherein the substantially noncompliant hoop is positioned in the first, middle lumen;
    further comprising:
        a split hoop positioned in the second lumen of the first, outer portion of the outer ring; and
        a split hoop positioned in the third lumen of the first, outer portion of the outer ring.

8. A surgical retractor for retracting an opening in a biological body wall, comprising,
    a substantially noncompliant outer ring having an annular axis and adapted for juxtaposition with an outer surface of the biological body wall, the outer ring comprising a first, outer portion having at least one lumen, and a substantially noncompliant hoop, the substantially noncompliant hoop being positioned in the at least one lumen of the first, outer portion, and the first, outer portion of the outer ring being made of materials that allow the outer ring to be turned around its annular axis;
    an inner ring adapted for juxtaposition with an inner surface of the biological body wall, the inner ring being made of materials having sufficient hardness to retain the shape of the inner ring after insertion of the inner ring into a body cavity; and
    a sleeve coupling the outer ring to the inner ring, the sleeve being adapted to traverse the opening in the body wall, the sleeve comprising a material that is flexible and impermeable to fluids and bacteria,
    wherein the substantially noncompliant outer ring being adapted to roll over itself around the annular axis to roll the sleeve around the outer ring to retract and seal the opening in the body wall;
    wherein the at least one lumen of the first, outer portion of the outer ring of the surgical retractor having two lumens, and further comprising:
    a substantially noncompliant hoop positioned in each of the two lumens of the first, outer portion of the outer ring of the surgical retractor, each of the substantially noncompliant hoops having a split.

9. The surgical retractor of claim 8, the outer ring having an oval cross-sectional shape.

10. The surgical retractor of claim 8, wherein:
    the substantially noncompliant outer ring being adapted to receive a lid coupled thereto, and
    the outer ring having a cross-sectional shape that facilitates proper coupling of the lid to the outer ring.

11. A surgical retractor for retracting an opening in a biological body wall, comprising,
    a substantially noncompliant outer ring having an annular axis and adapted for juxtaposition with an outer surface of the biological body wall, the outer ring comprising a first, outer portion having at least one lumen, and a substantially noncompliant hoop, the substantially noncompliant hoop being positioned in the at least one lumen of the first, outer portion, and the first, outer portion of the outer ring being made of materials that allow the outer ring to be turned around its annular axis;

an inner ring adapted for juxtaposition with an inner surface of the biological body wall, the inner ring being made of materials having sufficient hardness to retain the shape of the inner ring after insertion of the inner ring into a body cavity; and a sleeve coupling the outer ring to the inner ring, the sleeve being adapted to traverse the opening in the body wall, the sleeve comprising a material that is flexible and impermeable to fluids and bacteria, wherein the substantially noncompliant outer ring being adapted to roll over itself around the annular axis to roll the sleeve around the outer ring to retract and seal the opening in the body wall;

wherein the at least one lumen in the first, outer portion of the outer ring comprising:

a first, middle lumen;

a second, top lumen; and a third, bottom lumen, wherein the substantially noncompliant hoop of the outer ring being positioned in the first, middle lumen;

further comprising:

a split hoop positioned in the second lumen of the first, outer portion of the outer ring; and a split hoop positioned in the third lumen of the first, outer portion of the outer ring.

* * * * *